United States Patent
Kim et al.

(10) Patent No.: US 11,046,990 B2
(45) Date of Patent: Jun. 29, 2021

(54) INCREASED PRODUCTION OF GINSENOSIDES THROUGH IMPROVEMENT OF PROTEIN-FOLDING MACHINERY OF YEAST

(71) Applicants: INTELLIGENT SYNTHETIC BIOLOGY CENTER, Daejeon (KR); KOREA RESEARCH INSTITUTE OF CHEMICAL TECHNOLOGY, Daejeon (KR)

(72) Inventors: Sun-Chang Kim, Daejeon (KR); Ju Young Lee, Gyeonggi-do (KR); In Seung Jang, Busan (KR); Seohyun Kim, Busan (KR); Jong Geon Jegal, Ulsan (KR)

(73) Assignee: Korea Research Institute of Chemical Technology

( * ) Notice: Subject to any disclaimer, the term of this patent is extended or adjusted under 35 U.S.C. 154(b) by 110 days.

(21) Appl. No.: 16/057,617

(22) Filed: Aug. 7, 2018

(65) Prior Publication Data
US 2019/0048380 A1 Feb. 14, 2019

(30) Foreign Application Priority Data
Aug. 9, 2017 (KR) .................. 10-2017-0101319

(51) Int. Cl.
| | | |
|---|---|---|
| C12P 33/20 | (2006.01) | |
| C07K 14/415 | (2006.01) | |
| C12N 9/88 | (2006.01) | |
| C12N 9/04 | (2006.01) | |
| C12N 9/02 | (2006.01) | |

(52) U.S. Cl.
CPC ............ *C12P 33/20* (2013.01); *C07K 14/415* (2013.01); *C12N 9/0006* (2013.01); *C12N 9/0042* (2013.01); *C12N 9/0071* (2013.01); *C12N 9/88* (2013.01); *C12Y 101/01034* (2013.01); *C12Y 106/02004* (2013.01); *C12Y 114/14* (2013.01); *C12Y 402/01125* (2013.01)

(58) Field of Classification Search
CPC ......... C12P 33/20; C07K 14/415; C12N 9/88; C12N 9/0006; C12N 9/0071; C12N 9/0042; C12N 15/81; C12Y 402/01125; C12Y 106/02004; C12Y 101/01034; C12Y 114/14
See application file for complete search history.

(56) References Cited

FOREIGN PATENT DOCUMENTS

| JP | 2011-514157 A | 5/2011 |
|---|---|---|
| JP | 2015-509729 A | 4/2015 |
| JP | 2016-511639 A | 4/2016 |
| JP | 2016-514957 A | 5/2016 |
| KR | 10-2013-0137443 A | 12/2013 |
| WO | 2009105357 A1 | 8/2009 |
| WO | 2013183961 A1 | 12/2013 |
| WO | 2014138371 A1 | 9/2014 |

OTHER PUBLICATIONS

Ruijter et al. Enhancing antibody folding and secretion by tailoring the *Saccharomyces cerevisiae* endoplasmic reticulum. Microb Cell Facto (2016), 15:87, p. 1-18.*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36): 11643-50.*
Jorg C. De Ruijter et al., "Enhancing antibody folding and secretion by tailoring the *Saccharomyces cerevisiae* endoplasmic reticulum", Microbial Cell Fact, 2016, vol. 15, No. 87, pp. 1-18.
Lee et al., "Engineering Cellular Redox Balance in *Saccharomyces cerevisiae* for Improved Production of L-Lactic Acid", Biotechnology and Bioengineering, Apr. 2015, vol. 112, No. 4, pp. 751-758.
Office Action, Japanese Patent Office, Application No. 2018-149258, dated Jul. 23, 2019.
Tomas et al., "Overexpression of groESL in Clostridium acetobutylicum Results in Increased Solvent Production and Tolerance, Prolonged Metabolism, and Changes in the Cell's Transcriptional Program", Applied and Environmental Microbiology, Aug. 2003, pp. 4951-4965.
Liang, Hui-Chao et al., "Expression, subcellular localization and characterization of dammarenediol-II synthase of Panax ginsengin *Saccharomyces cerevisiae*", Acta Pharmaceutina Sinica, Jun. 30, 2016, pp. 998-1003.
Obel, Nicolai, Extended European Search Report, European Patent Office, Application No. 18187900.8, dated Sep. 18, 2018.
Wang, Le et al., "The isolation and characterization of dammarenediol synthase gene from Panax quinquefolius and its heterologous co-expression with cytochrome P450 gene PqD12H in yeast", Functional and Integrative Genomics, vol. 14, No. 3, Jun. 15, 2014, pp. 545-557.
Zhuang Yu et al., "Biosynthesis of plant-derived ginsenoside Rh2 in yeast via repurposing a key promiscuous microbial enzyme", Metabolic Engineering, vol. 42, May 4, 2017, pp. 25-32.

\* cited by examiner

*Primary Examiner* — Iqbal H Chowdhury
(74) *Attorney, Agent, or Firm* — Gavrilovich, Dodd & Lindsey LLP

(57) ABSTRACT

The present invention relates to recombinant yeast, in which the productivity of ginsenoside is enhanced by overexpressing CPR5, PDI1, or ERO1 in yeast having the productivity of ginsenosides; a method for preparing the yeast; and a method for producing ginsenosides using the yeast.

17 Claims, 4 Drawing Sheets

Specification includes a Sequence Listing.

INCREASED PRODUCTION OF GINSENOSIDES THROUGH IMPROVEMENT OF PROTEIN-FOLDING MACHINERY OF YEAST

CROSS REFERENCE TO RELATED APPLICATIONS

This application claims priority under 35 U.S.C. § 119 from Korean Patent Application No. 10-2017-0101319, filed Aug. 9, 2017, the disclosures of which are incorporated herein by reference.

TECHNICAL FIELD

The present invention relates to recombinant yeast for enhancing production of ginsenosides and a method for producing ginsenosides using the same.

BACKGROUND

Saponins, which are glycosides widely distributed in the plant kingdom, include diverse ring compounds formed in their non-sugar portions. Since triterpene saponins, which are contained in ginseng or red as major physiologically active ingredients, have a chemical structure different from saponins found in other plants, such ginseng saponins are called ginsenosides, meaning ginseng glycoside, named to distinguish them from other plant saponins.

Ginsenosides are classified into three groups based on their aglycone structure: protopanaxadiol (PPD)-type ginsenosides, protopanaxatriol (PPT)-type ginsenosides, and oleanolic acid-type ginsenosides. These three groups are further classified based on the position and number of sugar moieties attached by a glycosidic bond at C-3, C-6, and C-20 positions of the rings in the chemical structure (aglycone). The oleanolic acid-type ginsenoside has a pentacyclic backbone and ginsenoside Ro is the only saponin having oleanolic acid as its aglycone. To date, more than 40 ginsenosides have been isolated, and most of these are PPD-type ginsenosides. PPD-type ginsenosides include Rb1, Rb2, Rb3, Rc, Rd, gypenoside XVII, compound O, compound Mc1, F2, compound Y, compound Mc, Rg3, Rh2, and C-K. PPT-type ginsenosides include Re, Rg1, Rf, Rg2, Rh1, etc.

A representative pharmacological effect of ginseng is known to be exhibited by ginsenosides, and about 30 types of various ginsenosides have been isolated from ginseng and ginseng-processed products. In addition, it has been reported that ginsenosides have different pharmacological activities such as anti-diabetic activity, anti-inflammatory action, anti-aging action, anti-cancer action, etc. In addition, known physiologically active ingredients other than ginsenosides include phenolic components, polyacetylenes, alkaloids, polysaccharides, etc. Phenolic components are effective ingredients for inhibiting aging, and more than 10 kinds of antioxidant and phenolic materials have been identified. In addition, these are also known to have physiological activities such as anti-hypertensive, anti-cancer, antioxidant, and whitening activities. Recent studies have also shown that these have anti-stress effects that maintain nonspecific physical and mental stability against various stresses.

Globally, ginseng is cultivated commercially in South Korea, China, Japan, the United States, Canada, Europe, etc. By the end of 1980, South Korea, which produced about 46% of ginseng in the world, had decreased its market share to around 39% in the 1990s, while China accounts for more than 50% and North American ginseng produced in the United States and Canada accounts for 10%. Recently, Korea's market share of ginseng has decreased further. This is because although Korean ginseng is known to have a very excellent pharmacological effect, it is very weak in price competitiveness. Therefore, although Korean ginseng has numerous characteristics and merits, desperate efforts are necessary to improve the international competitiveness of Korean ginseng products due to the rapidly changing world, prior investment in bio-industry among nations, economic crises, etc.

Pharmacological studies of ginseng have increased the interest in ginsenosides, which are a component of ginseng, and the necessity for mass production thereof is emerging. However, since mass production of useful materials of ginseng through general cultivation methods has problems such as a long cultivation period of 4 years to 6 years, difficulty in controlling pests caused by shade cultivation, crop rotation cultivation, etc., development of a novel alternative production method is urgently required. Recently, many ginseng saponin-related genes have been discovered on the basis of biotechnology, and the development of a technique for mass-producing ginsenosides from yeast using these genes has recently begun to attract attention. Since ginsenosides are biosynthesized through the isoprenoid synthesis pathway, including the mevalonic acid biosynthetic pathway in plants, a synthetic biology study for developing ginsenoside-producing strains by redesigning the ergosterol biosynthetic pathway of yeast has been attempted. The Huang and Zhang collaborative research team in China has recently reported that the production of protopanaxadiol has been successful by expression of the protopanaxadiol dammarenediol-II synthase and protopanaxadiol synthase genes of ginsengs and the NADPH-cytochrome P450 reductase genes, which were obtained from *Arabidopsis thaliana*, in *Saccharomyces cerevisiae*. They overexpressed the N-terminal HMG gene (tHMG1) in order to amplify the supplies of squalene and 2,3-oxidosqualene. In addition, they also simultaneously overexpressed the FPP synthase gene (ERG20), the squalene synthase gene (EFG9), and the 2,3-oxidosqualene synthase gene (ERG1) to amplify the supply of precursors required for protopanaxadiol production. Additionally, according to yeast codons, the protopanaxadiol synthase gene was synthesized to further enhance the conversion efficiency of protopanaxadiol, and the uridine diphosphate glycosyl-transferase gene was introduced, and thereby a ginsenoside biosynthesis pathway was finally completed. Through optimization work, it is expected that in the future, ginsenoside-producing synthetic yeasts may provide an economical production process which can replace complex processes comprising a step of extraction from plants.

Under such circumstances, the present inventors have made extensive efforts to increase the amount of ginsenosides produced using yeasts, and as a result, they have developed recombinant yeast with an enhanced expression level of a protein involved in the protein folding of ginsenoside-producing yeast and a method for preparing the yeast. In addition, it was confirmed that in the recombinant yeast, the amount of protopanaxadiol production, which is an intermediate product in ginsenoside biosynthesis, was increased compared to existing yeast having the productivity of ginsenoside, and thereby the present inventors have completed the present invention.

DISCLOSURE

Technical Problem

An objective of the present invention is to provide recombinant yeast for producing ginsenosides or a precursor thereof.

Another objective of the present invention is to provide a method for preparing the recombinant yeast.

Still another objective of the present invention is to provide a method for producing ginsenosides or a precursor thereof in high yield using the recombinant yeast.

Technical Solution

Hereinafter, the present invention will be described in more detail. Meanwhile, each of the explanations and embodiments disclosed in the present invention can be applied to other explanations and embodiments. That is, all combinations of various elements disclosed in the present invention belong to the scope of the present invention. In addition, the specific descriptions hereinbelow should not be construed as limiting the scope of the present invention.

To achieve the above objectives, one aspect of the present invention provides recombinant yeast for producing ginsenoside or a precursor thereof, wherein the expression level of a protein involved in protein folding is enhanced relative to its endogenous expression level.

As used herein, the term "protein folding" refers to the process by which a protein, a linear amino acid complex, forms a folded structure or native structure. If the protein folding does not occur normally, accumulation of a protein that does not have normal folding would occur, which may induce endoplasmic reticulum stress. In response to this stress, an unfolded protein response (UPR) occurs.

The unfolded protein response includes (1) an increase of the protein-folding ability of an endoplasmic reticulum, (2) a decrease in protein uptake, and (3) decomposition of an unfolded protein. Therefore, the number of unfolded proteins in the endoplasmic reticulum may be reduced through the response above, and due to this, the unfolded protein response may also be reduced.

The present invention is characterized by increasing the production of ginsenosides or a precursor thereof by increasing the expression level of a protein involved in protein folding to increase the protein-folding ability of the endoplasmic reticulum and to reduce the unfolded protein response.

Specifically, the protein involved in protein folding may be a Chaperone protein.

As used herein, the term "Chaperone protein" is a protein that aids protein folding in cells. Most of the Chaperone proteins are expressed when exposed to heat or under stress, but can also be expressed under normal conditions to perform necessary functions. It is common that the Chaperon protein recognizes unfolded or misfolded proteins. Since various proteins exist in cells and the folding conditions of these proteins are different, there are various types of Chaperone proteins.

The exemplary embodiments of the present invention show that the production amounts of squalene, 2,3-oxidosqualene, and protopanaxadiol were increased as the endogenous expression level of the Chaperone protein involved in protein folding was enhanced (Example 3). Therefore, it was confirmed that the production of ginsenosides and a precursor thereof was increased through improvement of protein-folding machinery.

Specifically, the Chaperone protein involved in protein folding may include CPR5, PDI1, ERO1, KAR2, JEM1, LHS1, HSP82, YDJ1, SSA2, SSB1, GET3, SCJ1, FPR2, MPD1, etc., but is not limited thereto.

In an exemplary embodiment, the present invention provides recombinant yeast, wherein the protein involved in protein folding is one or more selected from the group consisting of CPR5, PDI1, and ERO1.

As used herein, the term "Cyclosporin-sensitive Proline Rotamase 5 (CPR5)" refers to peptidyl-prolyl cis-trans isomerase of the ER, which catalyzes the cis-trans isomerization of the N-terminal peptide bond at the proline residue. In addition, CPR5 is also induced in the ER by UPR. CPR5 is one of the Chaperone proteins involved in protein folding. Therefore, when unfolded proteins are accumulated in the ER, the amount of expression is increased to induce protein folding. CPR5 has CPR2 as an analogue.

The information on the CPR5 and the gene encoding the same can be obtained through a database such as the National Institutes of Health's GenBank. For example, the CPR5 gene may have the nucleotide sequence of SEQ ID NO: 1, but is not limited thereto.

Additionally, the gene encoding CPR5 includes not only the nucleotide sequence represented by SEQ ID NO: 1 but also any gene sequence having a sequence homology to the above nucleotide sequence of 80% or higher, specifically 90% or higher, more specifically 95% or higher, even more specifically 99% or higher, which encodes a transcription factor exhibiting effects that are substantially the same as or corresponding to that of the transcription factor of the CPR5, but the sequence is not limited thereto. In addition, in the case of the nucleotide sequences having such homology, it is obvious that the nucleotide sequences with a partial deletion, modification, substitution, or addition are included within the scope of the present invention.

As used herein, the term "Protein Disulfide Isomerase 1 (PDI1)" refers to multifunctional oxidoreductase of ER lumen and is essential for secretion and disulfide bonding in cell-surface proteins by rearranging non-native disulfide bonds. Additionally, it promotes endoplasmic-reticulum-associated protein degradation (ERAD), which removes unfolded proteins, by forming a complex with manoseidase-like protein 1 (MNL1) and treating Man8GlcNAc2 oligosaccharides, which are bound to an unfolded protein, with Man7GlcNAc2. The PDI1 has EUG1 as an analogue.

The information on the PDI1 and the gene encoding the same can be obtained through a database such as the National Institutes of Health's GenBank. For example, the PDI1 gene may have the nucleotide sequence of SEQ ID NO: 2, but is not limited thereto.

Additionally, the gene encoding PDI1 includes not only the nucleotide sequence represented by SEQ ID NO: 2 but also any gene sequence having a sequence homology to the above nucleotide sequence of 80% or higher, specifically 90% or higher, more specifically 95% or higher, even more specifically 99% or higher, which encodes a transcription factor exhibiting effects that are substantially the same as or corresponding to that of the transcription factor of the PDI1, but the sequence is not limited thereto. In addition, in the case of the nucleotide sequences having such homology, it is obvious that the nucleotide sequences with a partial deletion, modification, substitution, or addition are included within the scope of the present invention.

As used herein, the term "ER Oxidation or Endoplasmic Reticulum Oxidoreductin (ERO1)" refers to thiol oxidase required for oxidative protein folding in the ER, and is an enzyme essential for maintaining the balance of ER redox by regulated feedback through reduction and oxidation of regulatory binding. In addition, reduced Pdi1p activates Ero1p by direct reduction of Ero1p regulatory binding. Deficiency of a thiol substrate and accumulation of oxidized Pdi1p inactivate Ero1p by Pdi1p-mediated oxidation and spontaneous oxidation of Ero1p regulatory binding.

The information on the ERO1 and the gene encoding the same can be obtained through a database such as the National Institutes of Health's GenBank. For example, the ERO1 gene may have the nucleotide sequence of SEQ ID NO: 3, but is not limited thereto.

Additionally, the gene encoding ERO1 includes not only the nucleotide sequence represented by SEQ ID NO: 3 but also any gene sequence having a sequence homology to the above nucleotide sequence of 80% or higher, specifically 90% or higher, more specifically 95% or higher, even more specifically 99% or higher, which encodes a transcription factor exhibiting effects that are substantially the same as or corresponding to that of the transcription factor of the ERO1, but the sequence is not limited thereto. In addition, in the case of the nucleotide sequences having such homology, it is obvious that the nucleotide sequences with a partial deletion, modification, substitution, or addition are included within the scope of the present invention.

As used herein, the term "homology" refers to a degree of matching with a given amino acid sequence or nucleotide sequence, and the homology may be expressed as a percentage. In the present invention, a homology sequence having an activity which is identical or similar to the given amino acid sequence or nucleotide sequence is expressed as "% homology". The homology sequence may be determined by, for example, standard software, specifically, BLAST 2.0, which calculates the parameters such as score, identity, similarity, etc., or by comparing the sequences in a Southern hybridization experiment under defined stringent conditions, and defining appropriate hybridization conditions are within the skill of the art, and may be determined by a method well known to those skilled in the art.

As used herein, the term "endogenous expression level" refers to an expression level of mRNA or a protein expressed in a parent strain in which the natural state or the expression level of a gene of interest has not been transformed in a microorganism. In addition, such expression level is essentially the degree of production of given mRNA or protein in cells and tissues under normal conditions or conditions where regulation of the expression of a specific gene has not been performed. The endogenous expression level can be compared between the strain type, cell type, and tissues; or can be compared with expression levels induced by some stimuli. Specifically, the endogenous expression level may be an expression level of mRNA or a protein expressed in a microorganism that does not regulate expression of a protein involved in protein folding.

As used herein, the expression "expression level is enhanced relative to its endogenous expression level" means that a gene encoding a polypeptide of interest is more expressed compared to that in a natural state or a state before modification, thereby producing a large number of the functional polypeptide of interest.

Specifically, in the present invention, the enhancement of expression levels of CPR5, PDI1, and ERO1 may be conducted by the following methods:

1) increasing the copy number of a polynucleotide encoding the proteins;
2) modification of an expression regulatory sequence for enhancing the polynucleotide expression;
3) modification of the polynucleotide sequence on a chromosome for enhancing activities of the proteins; or
4) a combination thereof, but the methods are not limited thereto.

In method 1), the increase of the copy number of the polynucleotide encoding the proteins may be achieved by operably linking the polynucleotide to the vector, or by inserting the same into the chromosome of the host cell, but is not limited thereto. Specifically, the increase of the copy number of a polynucleotide may be performed by introducing into a host cell a vector to which the polynucleotide encoding the enzymes of the present invention is operably linked that can replicate and function regardless of a host. Alternatively, the increase of the copy number of a polynucleotide may be performed by introducing into a host cell a vector to which the polynucleotide is operably linked that can insert the polynucleotide into the chromosome of the host cell, thereby increasing the copy number of the polynucleotide in the chromosome of the host cell.

As used herein, the term "vector" refers to a DNA construct including the nucleotide sequence of the polynucleotide encoding a target protein, in which the target protein is operably linked to a suitable control sequence so that it can be expressed in an appropriate host. The control sequence includes a promoter capable of initiating transcription, any operator sequence for the control of the transcription, a sequence encoding an appropriate mRNA ribosome-binding domain, and a sequence controlling the termination of transcription and translation. The vector, after being transformed into a suitable host cell, may be replicated or function irrespective of the host genome, or may be integrated into the host genome itself.

The vector used in the present invention may not be particularly limited as long as the vector is able to replicate in a host cell, and any vector known in the art may be used. Examples of the vector may include natural or recombinant plasmids containing replication origin, a promoter, and a terminator. The replication origin may include a yeast autonomous replication sequence (ARS). The yeast autonomous replication sequence may be stabilized by a yeast centrometric sequence (CEN). The promoter may be selected from the group consisting of a CYC promoter, a TEF promoter, a GPD promoter, a PGK promoter, an ADH promoter, etc. The terminator may be selected from the group consisting of PGK1, CYC1, GAL1, etc. The vector may further comprise a selective marker.

Additionally, the polynucleotide encoding the target protein can be replaced with a modified polynucleotide within the chromosome by a vector for the insertion of a chromosome within cells. The insertion of the polynucleotide into the chromosome may be performed using any method known in the art, for example, by homologous recombination, but the method is not limited thereto.

As used herein, the term "transformation" means the introduction into a host cell of a vector including a polynucleotide encoding a target protein in such a way that the protein encoded by the polynucleotide is expressed in the host cell. As long as the transformed polynucleotide can be expressed in the host cell, it can be either integrated into and placed in the chromosome of the host cell, or exist extra-chromosomally. Further, the polynucleotide includes DNA and RNA encoding the target protein. The polynucleotide may be introduced in any form, as long as it can be introduced into the host cell and expressed therein. For example, the polynucleotide may be introduced into the host cell in the form of an expression cassette, which is a gene construct including all elements required for its autonomous expression. Typically, the expression cassette includes a promoter operably linked to the polynucleotide, transcriptional termination signals, ribosome binding sites, or translation termination signals. The expression cassette may be in the form of a self-replicable expression vector. Also, the polynucleotide may be introduced into the host cell as-is and operably linked to sequences required for expression in the host cell, but is not limited thereto.

Further, as used herein, the term "operably linked" refers to a functional linkage between a polynucleotide sequence encoding the desired protein of the present invention and a promoter sequence which initiates and mediates transcription of the polynucleotide sequence.

Next, 2) modification of the expression regulatory sequence for increasing the polynucleotide expression may be, but is not particularly limited to, done by inducing a modification on the expression regulatory sequence through deletion, insertion, non-conservative or conservative substitution of a nucleotide sequence, or a combination thereof in order to further enhance the activity of the expression regulatory sequence, or by replacing the expression regulatory sequence with a nucleotide sequence having stronger activity. The expression regulatory sequence includes, but is not particularly limited to, a promoter, an operator sequence, a sequence coding for a ribosome-binding site, and a sequence regulating the termination of transcription and translation.

A strong heterologous promoter may be linked upstream of the polynucleotide expression unit instead of the original promoter, and examples of the strong promoter may include a GPD promoter, a TEF promoter, an ADH promoter, a CCW12, a GAL promoter, a PGK promoter, etc., and specifically, a PGK1 promoter, which is a *Saccharomyces cerevisiae*-derived promoter, is operably linked to the polynucleotide encoding the enzyme so that its expression rate may be increased, but is not limited thereto.

Furthermore, 3) modification of a polynucleotide sequence on chromosome, although not particularly limited thereto, may be performed by inducing a mutation on the expression regulatory sequence through deletion, insertion, non-conservative or conservative substitution of a polynucleotide sequence, or a combination thereof in order to further enhance the activity of the polynucleotide sequence, or by replacing the sequence with a polynucleotide sequence which is modified to have stronger activity.

In an exemplary embodiment of the present invention, in order to induce overexpression of CPR5, PDI1, or ERO1, a PGK1 promoter replacement vector was constructed for substituting the promoter of the gene with a PGK1 promoter, which is a strong constitutive promoter, and then the substitution cassette constructed using the vector was transfected into a modified PPD yeast strain, and thereby recombinant yeast overexpressing CPR5, PDI1, or ERO1 was prepared (Example 2).

According to a specific exemplary embodiment, the amounts of squalene, 2,3-oxidosqualene, and protopanaxadiol, which are intermediate products in ginsenoside biosynthesis, produced using the recombinant yeast were measured and compared with a control group. As a result, it was confirmed that the production amounts were increased in the recombinant yeast in which CPR5, PDI1, or ERO1 is overexpressed, compared to the control group. It was also confirmed that, in particular, the production amounts were mostly increased in the recombinant yeast in which CPR5 or ERO1 is overexpressed (Example 3, Tables 3 and 4, and FIG. 4).

The recombinant yeast of the present invention can increase the production amounts of ginsenoside, squalene, and 2,3-oxidosqualene.

As used herein, the term "recombinant yeast for producing ginsenoside" refers to yeast which naturally has the ginsenoside-producing ability or yeast in which the ginsenoside-producing ability is given to a parent strain not having the ginsenoside-producing ability.

As used herein, the term "ginsenoside" refers to a dammarane-type saponin derived from ginseng or a derivative thereof, and has a unique chemical structure different from that of saponins found in other plants. The ginsenoside may be, for example, a protopanaxadiol (PPD)-type ginsenoside, a protopanaxatriol (PPT)-type ginsenoside, etc., but is not limited thereto. In another example, PPD, PPT, Ra3, Rb1, Rb2, Rb3, Rc, Rd, Re, Rg1, Rg2, Rg3, Rh1, Rh2, Rs1, C-O, C-Y, C-Mc1, C-Mc, F1, F2, compound K, gypenoside XVII, gypenoside LXXV, Rs2, PPD, Re, Rg1, Rf, F1, Rg2, PPT, and Rh1 may be used alone or as a mixture thereof. In still another example, PPD, PPT, compound K, Rb1, Rb2, Rb3, Rc, Rd, Re, F1, F2, Rg1, Rg2, Rg3, Rh1, and Rh2 may be used alone or as a mixture thereof. Specifically, the ginsenoside may be a protopanaxadiol-type ginsenoside.

As used herein, the term "recombinant yeast for producing a ginsenoside precursor" refers to yeast which naturally has the ginsenoside precursor-producing ability or yeast in which the ginsenoside precursor-producing ability is given to a parent strain not having the ginsenoside-producing ability.

As used herein, the term "ginsenoside precursor" refers to an intermediate product of a metabolism process for ginsenoside biosynthesis. In the ginsenoside biosynthesis, isopentenyl diphosphate and dimethylallyl diphosphate are produced, and these are transformed to squalene and 2,3-oxidosqualene into which squalene is oxidized. The cyclization of 2,3-oxidosqualene produces dammarenediol-II, which can be synthesized into several ginsenosides. The ginsenoside precursor may include all of these intermediate products. In addition, other types of saponins produced though the precursor may be included. The ginsenoside precursor may additionally include β-amyrin or oleanate.

Specifically, the recombinant yeast for producing the ginsenoside precursor may produce squalene or 2,3-oxidosqualene.

A specific embodiment of the present invention provides recombinant yeast, wherein the ginsenoside precursor comprises squalene and 2,3-oxidosqualene.

As used herein, the term "squalene" belongs to the group of isoprenoids or terpenoids, and is a polyunsaturated lipid ($C_{30}H_{50}$) with six double bonds. Squalene is an intermediate product in ginsenoside biosynthesis, and is produced via the mevalonic acid pathway. Squalene also has a strong antioxidant activity in vivo, and used for biosynthesis of steroid hormones, vitamin D, bile acid, and cholesterol, which is a component of cell membranes. In addition, squalene can also be used as a vaccine adjuvant for treating swine flu, etc.

As used herein, the term "2,3-oxidosqualene" refers to a synthetic precursor of the cell membrane sterol precursors lanosterol and cycloartenol, as well as saponins including ginsenosides. 2,3-Oxidosqualene is produced by the oxidation of squalene by squalene epoxidase.

The yeast may be a strain belonging to *Saccharomyces, Zygosaccharomyces, Pichia, Kluyveromyces, Candida, Shizosaccharomyces, Issachenkia, Yarrowia*, or *Hansenula*.

The strain belonging to *Saccharomyces* may be, for example, *S. cerevisiae, S. bayanus, S. boulardii, S. bulderi, S. cariocanus, S. cariocus, S. chevaliers, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum*, or *S. zonatus*.

In a specific embodiment of the present invention, the yeast may be Saccharomyces cerevisiae (S. cerevisiae), but is not limited thereto.

In general, S. cerevisiae is known as a yeast used in various fermentation processes, and is also known to have an activity of converting sugar to ethanol.

In the yeast producing ginsenosides, in order to enhance the metabolic pathway of mevalonic acid to increase the biosynthesis of squalene, a precursor essential for ginsenoside biosynthesis, HMG-CoA reductase (tHMG1), which converts HMG-CoA to mevalonic acid, and Panax ginseng squalene epoxidase (PgSE), which converts squalene to 2,3-oxidosqualene, may be modified to increase their activities compared to their endogenous activities; and in order to introduce the metabolic pathway of ginsenoside biosynthesis, Panax ginseng dammarenediol-II synthase (PgDDS), which converts 2,3-oxidosqualene to dammarenediol-II, Panax ginseng cytochrome P450 CYP716A47 (PgPPDS), which converts dammarenediol-II to protopanaxadiol, and Panax ginseng NADPH-cytochrome P450 reductase (PgCPR) may be modified to introduce their activities, but these are not particularly limited thereto.

Another specific embodiment of the present invention provides recombinant yeast, wherein the expression level of the gene involved in ginsenoside synthesis is further increased compared to its endogenous expression level.

Still another specific embodiment of the present invention provides recombinant yeast, wherein the gene is one or more selected from the group consisting of Panax ginseng dammarenediol-II synthase (PgDDS), Panax ginseng cytochrome P450 CYP716A47 (PgPPDS), Panax ginseng NADPH-cytochrome P450 reductase (PgCPR), S. cerevisiae HMG-CoA reductase (tHMG1), and Panax ginseng squalene epoxidase (PgSE).

In an embodiment of the present invention, the enzyme involved in the metabolic pathway of ginsenoside synthesis was introduced by transformation, and the enzyme involved in the metabolic pathway of mevalonic acid was transcribed from a GPD1 (TDH3) promoter, which is a strong constitutive promoter, and thereby their expressions were enhanced compared to their endogenous expressions (Example 1).

Herein, each of the enzymes involved in the metabolic pathway of ginsenoside biosynthesis may include the amino acid sequence of SEQ ID NOS: 4 to 8 or the amino acid sequence having a homology to the above sequence of 70% or higher, specifically 80% or higher, more specifically 90% or higher.

Another aspect of the present invention provides a method for preparing recombinant yeast with an enhanced productivity of ginsenosides, comprising increasing the expression level of a protein involved in protein folding in a ginsenoside-producing yeast strain relative to its endogenous expression level.

One specific embodiment of the present invention provides a method for preparing recombinant yeast, wherein the protein involved in protein folding is one or more selected from the group consisting of CPR5, PDI1, and ERO1.

The ginsenoside-producing yeast strain, the protein involved in protein folding, CPR5, PDI1, ERO1, and the endogenous expression are as described above.

In another specific embodiment of the present invention, the ginsenoside-producing yeast strain may be one or more selected from the group consisting of Panax ginseng dammarenediol-II synthase (PgDDS), Panax ginseng cytochrome P450 CYP716A47 (PgPPDS), Panax ginseng NADPH-cytochrome P450 reductase (PgCPR), S. cerevisiae HMG-CoA reductase (tHMG1), and Panax ginseng squalene epoxidase (PgSE), in which the expression levels of the genes are enhanced compared to their endogenous expression level.

Still another aspect of the present invention provides a method for preparing recombinant yeast with an enhanced productivity of ginsenoside precursor, comprising increasing the expression level of a protein involved in protein folding in a ginsenoside precursor-producing yeast strain relative to its endogenous expression level.

A specific embodiment of the present invention provides a method for preparing recombinant yeast, wherein the ginsenoside precursor comprises squalene or 2,3-oxidosqualene.

Another specific embodiment of the present invention provides a method for preparing recombinant yeast, wherein the protein involved in protein folding is one or more selected from the group consisting of CPR5, PDI1, and ERO1, in which their expression levels are increased compared to their endogenous expression levels.

The protein involved in protein folding, CPR5, PDI1, ERO1, and the endogenous expression level are as described above.

Still another aspect of the present invention provides a method for producing ginsenosides or a precursor thereof, comprising culturing the recombinant yeast.

In the method, culturing the enzymes may preferably be done by batch culture, continuous culture, and fed-batch culture known in the art, but is not particularly limited thereto. Furthermore, as for the culturing condition, an optimal pH of 5 to 9, specifically pH 6 to 8, and most specifically pH 6.8 can be maintained by using a basic compound (for example: sodium hydroxide, potassium hydroxide, or ammonia) or an acidic compound (for example: phosphoric acid or sulfuric acid), but the culturing conditions are not particularly limited thereto. In addition, an aerobic condition can be maintained by adding oxygen or an oxygen-containing gas mixture to a cell culture. The culturing temperature may be maintained at 20° C. to 45° C., and specifically at 25° C. to 40° C. Further, it is preferable to culture for about 10 hours to 160 hours. The ginsenoside produced by the above culturing may be excreted to a culture medium or remain inside the cell.

Furthermore, the medium for culturing may comprise sugars and carbohydrates (for example: glucose, sucrose, lactose, fructose, maltose, molasses, starch, and cellulose), oils and fats (for example: soybean oil, sunflower seed oil, peanut oil, and coconut oil), fatty acids (for example: palmitic acid, stearic acid, and linoleic acid), alcohols (for example: glycerol and ethanol), and organic acids (for example: acetic acid) individually or in combination as a carbon source; nitrogen-containing organic compounds (for example: peptone, yeast extract, meat juice, malt extract, corn solution, soybean meal powder, and urea), or inorganic compounds (for example: ammonium sulfate, ammonium chloride, phosphate, or ammonium, ammonium carbonate, and ammonium nitrate) individually or in combination as a nitrogen source; potassium dihydrogen phosphate, dipotassium phosphate, or a sodium-containing salt corresponding thereto individually or in combination as a phosphorus source; other essential growth-stimulating substances including metal salts (for example: magnesium sulfate or iron sulfate), amino acids, and vitamins, but these are not limited thereto.

The method may further include a step of recovering the ginsenoside produced. This recovery step may be a step of recovering from the cultured cell or its supernatant, and those skilled in the art may select an appropriate procedure for the recovery.

The method of for recovering the ginsenoside produced from the recovery step of the present invention can be performed by collecting the desired product from the culture medium using a suitable method selected depending on the culture method such as a batch, continuous, or fed-batch culture method.

Advantageous Effects

The recombinant yeast of the present invention with an enhanced productivity of ginsenoside may be one or more selected from the group consisting of CPR5 having the nucleotide sequence of SEQ ID NO: 1, PDI1 having the nucleotide sequence of SEQ ID NO: 2, or ERO1 having the nucleotide sequence of SEQ ID NO: 3, and it is modified to have an expression level increased compared to its endogenous expression level. As a result, the ability of producing ginsenosides is enhanced, and thus the recombinant yeast of the present invention can be effectively used for ginsenoside production.

DETAILED DESCRIPTION

Hereinbelow, the present invention will be described in detail with accompanying exemplary embodiments. However, the exemplary embodiments disclosed herein are only for illustrative purposes and should not be construed as limiting the scope of the present invention.

Example 1: Construct of PPD Modified Yeast Strain

In *S. cerevisiae* CEN.PK2-1D wild-type strains [(MATα ura3-52; trp1-289; leu2-3,112; his3Δ1; MAL2-8; SUC2), EUROSCARF accession number: 30000B], the metabolic pathway of ginsenoside biosynthesis was introduced and the metabolic pathway of mevalonic acid for enhancing the biosynthesis of squalene was enhanced, which is a precursor essential for ginsenoside biosynthesis. Thereafter, the yeast strain producing protopanaxadiol (PPD) was constructed, and this yeast strain was named as a modified PPD yeast strain.

The genotype of the PPD strain is *S. cerevisiae* CEN.PK2-1D Δtrp1::$P_{GPD1}$ tHMG1+$P_{GPD1}$ PgSE+Δleu2::$P_{GPD1}$ PgDDS+$P_{GPD1}$ PgPPDS+$P_{GPD1}$ PgCPR. Genes encoding Panax ginseng dammarenediol-II synthase (PgDDS; SEQ ID NO: 4), Panax ginseng cytochrome P450 CYP716A47 (PgPPDS; SEQ ID NO: 5), and Panax ginseng NADPH-cytochrome P450 reductase (PgCPR; SEQ ID NO: 6), which are ginsenoside biosynthetic enzymes, and genes encoding *S. cerevisiae* HMG-CoA reductase (tHMG1; SEQ ID NO: 7) and Panax ginseng squalene epoxidase (PgSE; SEQ ID NO: 8), which are enzymes for enhancing the metabolic pathway of mevalonic acid, were each transcribed from the GPD1 (TDH3) promoter, which is a strong constitutive promoter, so as to be expressed.

Example 2: Construct of CPR5-, PDI1-, or ERO1-Overexpressing Modified Yeast Strain In the modified PPD yeast strain, in order to confirm whether overexpression of CPR5, PDI1, or ERO1, which are proteins involved in protein folding, is involved in the growth of the modified yeast strain and the PPD-producing ability, the modified yeast strain was constructed in which CPR5, PDI1, or ERO1 gene is overexpressed. First, in order to induce overexpression of the CPR5, PDI1, or ERO1 gene, a PGK1 promoter replacement vector was constructed for substituting the promoter of the gene to a PGK1 promoter, which is a strong constitutive promoter, and then the substitution cassette constructed using the vector was transfected into the modified PPD yeast strain, and thereby a modified yeast strain overexpressing CPR5, PDI1, or ERO1 was constructed.

Figure 1:
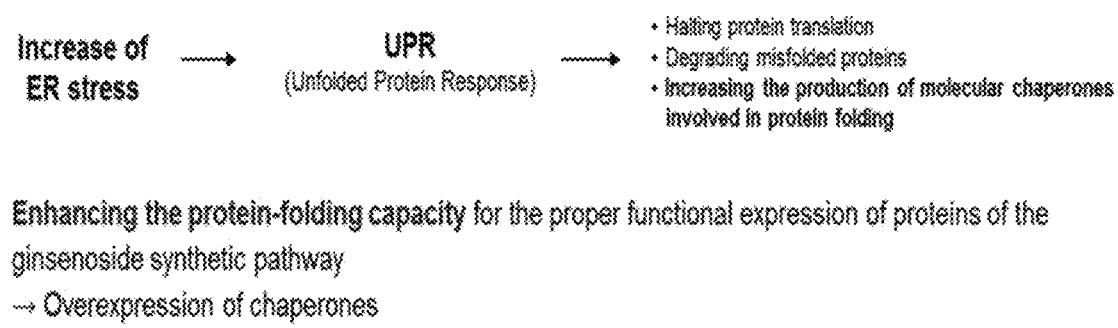
FIG. 1 is a simplified illustration of an increase in the production amount of ginsenosides through improved protein folding.
Figure 2:
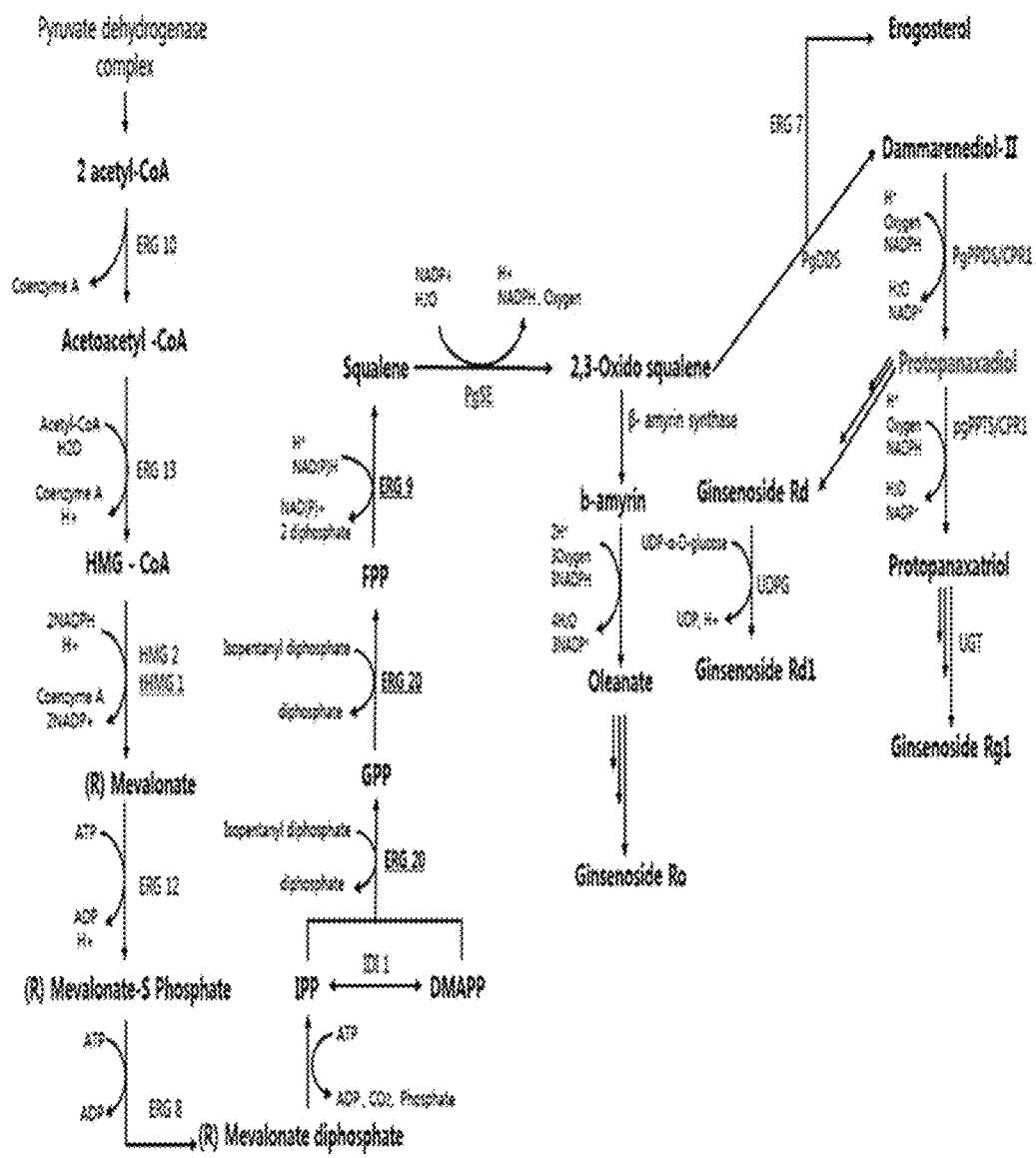
FIG. 2 is diagram showing a metabolic pathway of ginsenoside biosynthesis.
Figure 3:
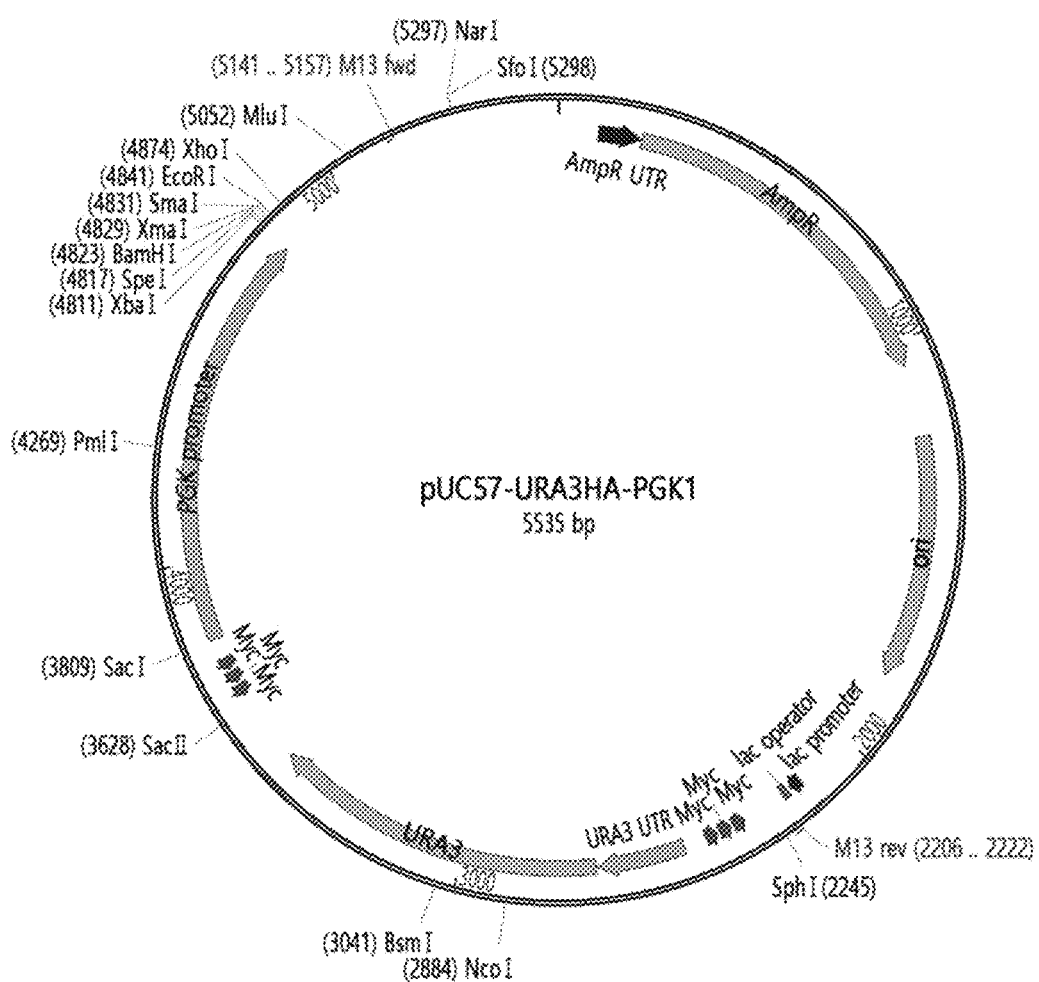
FIG. 3 is a diagram showing a vector map of pUC57-URA3HA-PGK1, which is a vector prepared for overexpressing the CPR5, PDI1, or ERO1 gene.

Specifically, in order to construct the PGK1 promoter replacement vector, target fragments were obtained by PCR amplification from the genomic DNA of *S. cerevisiae* CEN.PK2-1 using primers in a combination of PGK1 pro F and PGK1 pro R primers (Table 1), such that the sequence of a site of the PGK1 promoter (i.e., a strong constitutive promoter) has recognition sites for restriction enzymes SacI and XbaI at the 5' and 3' sites of the promoter, respectively, followed by conducting electrophoresis of the amplified PCR fragments. Herein, the PCR was carried out for a total of 25 cycles under the following conditions: denaturation at 95° C. for 30 seconds, annealing at 56° C. for 30 seconds, and elongation at 72° C. for 30 seconds. The amplified fragments were treated with SacI and XbaI, and then inserted into a pUC57-URA3HA vector treated with the same restriction enzymes. Engineering cellular redox balance in *Saccharomyces cerevisiae* for improved production of L-lactic acid. *Biotechnol. Bioeng.,* 112, 751-758.), thereby constructing a pUC57-URA3HA-PGK1 vector (SEQ ID NO: 9) (FIG. 3).

The primer sequences and restriction enzymes used for constructing the pUC57-URA3HA-PGK1 vector are shown in Table 1 below.

TABLE 1

| Primer | Primer Sequence | SEQ ID NO | Restriction Enzyme |
|---|---|---|---|
| PGK1 pro F | 5'-CGAGCTCAGACGCGAATTTTTCGGG-3' | 10 | SacI |
| PGK1 pro R | 5'-GACTAGTTCTAGATGTTTTATATTTGTTGTAAAA AGTAGATAATTACTTCC-3' | 11 | XbaI |

PCR was carried out with primers in a combination of P_CPR5 F and P_CPR5 R (SEQ ID NOS: 12 and 13), which have the homologous recombination sequences to the CPR5 promoter sites, using the thus-prepared pUC57-URA3HA-PGK1 vector as a template. Similarly, the cassette substituting the CPR5 promoter with the PGK1 promoter was constructed. In addition, PCR was carried out with primers in a combination of P_PDI1 F and P_PDI1 R (SEQ ID NOS: 14 and 15), which have the homologous combination sequences to the PDI1 promoter sites, to construct the cassette substituting the PDI1 promoter with the PGK1 promoter. In addition, PCR was carried out with primers in a combination of P_ERO1 F and P_ERO1 R (SEQ ID NOS: 16 and 17), which have the homologous sequences to the ERO1 promoter sites, to construct the cassette constituting the ERO1 promoter with the PGK1 promoter. Herein, the PCR was carried out for a total of 25 cycles under the following conditions: denaturation at 95° C. for 30 seconds, annealing at 56° C. for 30 seconds, and elongation at 72° C. for 2 minutes.

The thus-prepared cassette for substituting the CPR5 promoter, PDI1 promoter, or ERO1 promoter was each introduced into the modified PPD yeast strain. The introduction was carried out by a common heat shock transformation. After the transformation, cells were cultured in uracil dropout medium (yeast nitrogen base without amino acids 6.7 g, CSM minus uracil 0.77 g, glucose 20 g, 1 L), and the CPR5 promoter, PDI1 promoter, or ERO1 promoter on the genome was allowed to be substituted with the PGK1 promoter by each of the cassettes above.

In order to confirm whether each of the promoters was substituted with the PGK1 promoter in the thus-obtained modified yeast strain, PCR was carried out with primers in a combination of CPR5 to PGK1 F and CPR5 to PGK1 R (SEQ ID NOS: 18 and 19) using the genome of the cells above as a template; as a result, it was confirmed that CPR5 promoter was substituted with the PGK1 promoter. In addition, PCR was carried out with primers in a combination of PDI1 to PGK1 F and PDI1 to PGK1 R (SEQ ID NOS: 20 and 21) or a combination of ERO1 to PGK1 F and ERO1 to PGK1 R (SEQ ID NOS: 22 and 23), and as a result, it was confirmed that the PDI1 promoter or the ERO1 promoter was substituted with the PGK1 promoter. Based on the results above, PPD-CPR5($P_{CPR5}$::$P_{PGK1}$), PPD-PDI1 ($P_{PDI1}$::$P_{PGK1}$), and PPD-ERO1($P_{ERO1}$::$P_{PGK1}$) modified yeast strains were prepared.

The primer sequences for preparing the PGK1 promoter substitution cassette and for confirming the substitution are shown in Table 2 below.

TABLE 2

| Primer | Primer Sequence | SEQ ID NO |
|---|---|---|
| P_CPR5 F | 5'-ACTAGAAGAATTTGTATCTTCTGATCCTGGTTTAACACA ATGGTTATAGTAGGTTTCCCGACTGGAAAGC-3' | 12 |
| P_CPR5 R | 5'-GTGAAGAGACAAGCAAATAAGGTAATAAAGGAAAAAAAT TGAAGCTTCATTGTTTTATATTTGTTGTAGTAGATAA-3' | 13 |
| P_PDI1 F | 5'-CTTATAATGCGGGGTGCAAGCGCCGCGTCTAAAATTTTT TTTTTTTCCATAGGTTTCCCGACTGGAAAGC-3' | 14 |
| P_PDI1 R | 5'-GCGAGCAGCAGGGAGGACCATGACAGGACGGCACCAGCA GAAAACTTcatTGTTTTATATTTGTTGTAGTAGATAA-3' | 15 |
| P_ERO1 F | 5'-GTAAAATTGTACATTATTTATTTCTATATAACAGG ATCCCTCCAGTAGGTTTCCCGACTGGAAAGC-3' | 16 |
| P_ERO1 R | 5'-GATGTAAAAGCCGTGAGGCACAGTGTGGCAATGGCGGT TCTTAATCTCATTGTTTTATATTTGTTGTAGTAGATAA-3' | 17 |
| CPR5 to PGK1 F | 5'-TCTTCTGATCCTGGTTTAACACAATGG-3' | 18 |
| CPR5 to PGK1 R | 5'-CTTTCGCTGGCTGTTGTGAA-3' | 19 |
| PDI1 to PGK1 F | 5'-AAGCGCCGCGTCTTTT-3' | 20 |
| PDI1 to PGK1 R | 5'-GGGAGGACCATGACAGGACG-3' | 21 |
| ERO1 to PGK1 F | 5'-GTGCTGTGTACACCCGTAAAATTGT-3' | 22 |
| ERO1 to PGK1 R | 5'-GAGGCACAGTGTGGCAATGG-3' | 23 |

Example 3: Confirmation of Growth of Transformed, Modified Yeast Strain and Amount of PPD Production The transformed, modified yeast strains prepared above were inoculated into minimal URA drop-out media (50 mL) containing 2% glucose such that the $OD_{600}$ became 0.5. Thereafter, the resultants were cultured under aerobic conditions for 144 hours while stirring at 30° C. at 250 rpm. The $OD_{600}$ value of the cell growth during the culture was measured using a spectrophotometer. The intracellular metabolites (e.g., squalene, 2,3-oxidosqualene, and protopanaxadiol) during the culture were analyzed using high-performance liquid chromatography (HPLC).

Figure 4:
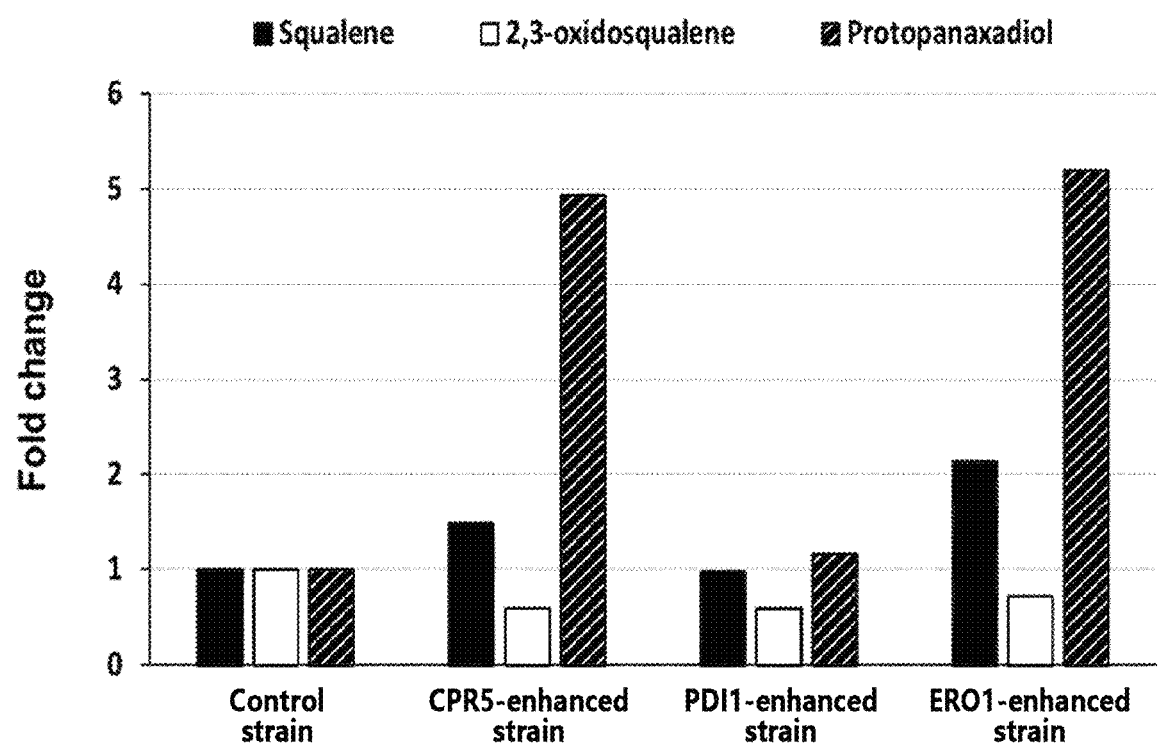
FIG. 4 is a graph showing the amounts of squalene, 2,3-oxidosqualene, and protopanaxadiol productions in comparison with a control group, when CPR5, PDI1, or ERO1 are overexpressed.

As a result of culturing for 72 hours and 144 hours, the cell growths, i.e., the $OD_{600}$ value of the culture and the concentrations of each intracellular metabolite, are as shown in Tables 3, 4, and FIG. 4.

The concentrations of the metabolites according to the culture of the transformed, modified yeast strains prepared above are shown in Table 3 below.

TABLE 3

| Strain | Cell Growth (OD$_{600}$) | | Amount of Metabolite Production (mg/L) | | | | | |
|---|---|---|---|---|---|---|---|---|
| | | | Squalene | | 2,3-oxidosqualene | | Protopanaxadiol | |
| | 72 h | 144 h | 72 h | 144 h | 72 h | 144 h | 72 h | 144 h |
| Control | 17.44 | 15.69 | 0.19 | 1.13 | 0.64 | 0.69 | 0.25 | 1.67 |
| CPR5-overexpressing strain | 18.65 | 15.86 | 0.96 | 1.67 | 0.87 | 0.41 | 1.35 | 8.25 |
| PDI1-overexpressing strain | 17.24 | 16.27 | 0.69 | 1.09 | 0.80 | 0.41 | 0.42 | 1.93 |
| ERO1-overexpressing strain | 18.98 | 16.93 | 0.80 | 2.41 | 1.82 | 0.49 | 1.02 | 8.68 |

The values of the concentrations multiples of the metabolites according to the cultures of the transformed, modified yeast strains prepared above are shown in Table 4 below.

TABLE 4

| Strain | Squalene | 2,3-oxidosqualene | Protopanaxadiol |
|---|---|---|---|
| Control | 1 | 1 | 1 |
| CPR5-overexpressing strain | 1.48 | 0.59 | 4.93 |
| PDI1-overexpressing strain | 0.97 | 0.59 | 1.15 |
| ERO1-overexpressing strain | 2.14 | 0.72 | 5.19 |

In Tables 3 and 4, the control group represents the modified PPD yeast strain (*S. cerevisiae* CEN.PK2-1D Δtrp1::tHMG1+P$_{GPD1}$ PgSE+Δleu2::P$_{GPD1}$ PgDDS+P$_{GPD1}$ PgPPDS+P$_{GPD1}$ PgCPR); the CPR5-enhanced strain represents PPD-CPR5(P$_{CPR5}$::P$_{PGK1}$); the PDI1-enhanced strain represents PPD-PDI1(P$_{PDI1}$::P$_{PGK1}$); and the ERO1-enhanced strain represents PPD-ERO1(P$_{ERO1}$::P$_{PGK1}$).

The values in Table 4 indicate multiple values of the metabolites produced from each of the modified yeast strains which had been prepared, wherein the value of the concentration of each of the metabolites (e.g., squalene, 2,3-oxidosqualene, and protopnanxadiol) is set to 1.

Based on the results above, it was confirmed that the transformation of the modified yeast strains had no significant effect on the cell growth. In addition, as a result of the measurement of the concentrations of the intracellular metabolites, it was confirmed that overexpression of CPR5, PDI1, or ERO1 increases the protein folding, thereby increasing the concentrations of the metabolites of ginsenoside biosynthesis through a decrease in the unfolded protein response (UPR). Therefore, based on these results, it can be predicted that the ginsenoside-producing ability is finally improved.

The invention claimed is:

1. A recombinant yeast for producing a ginsenoside or a precursor thereof, wherein the recombinant yeast expresses a polynucleotide that encodes a protein involved in protein folding having at least 95% sequence homology to SEQ ID NO:1 or SEQ ID NO:3,
wherein the protein involved in protein folding has Cyclosporin-sensitive Proline Rotamase 5 (CPR5)-like activity, or ER Oxidation or Endoplasmic Reticulum Oxidoreductin (ERO1)-like activity;
wherein the recombinant yeast has elevated expression levels of the protein involved in protein folding in comparison to endogenous expression levels of the protein; and
wherein the recombinant yeast comprises ginsenoside synthesizing genes encoding the proteins of HMG-CoA reductase (tHMG1), Panax ginseng squalene epoxidase (PgSE), Panax ginseng dammarenediol-ll synthase (PgDDS), Panax ginseng cytochrome P450 CYP716A47 (PgPPDS), and Panax ginseng NADPH-cytochrome P450 reductase (PgCPR).

2. The recombinant yeast of claim 1, wherein the polynucleotide has at least 99% sequence homology to SEQ ID NO:1 and the protein involved in protein folding has CPR5-like activity.

3. The recombinant yeast of claim 1, wherein the polynucleotide has at least 99% sequence homology to SEQ ID NO:3 and the protein involved in protein folding has ERO1-like activity.

4. The recombinant yeast of claim 1, wherein the yeast is selected from the group consisting of S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum, and S. zonatus.

5. The recombinant yeast of claim 1, wherein the expression levels of tHMG1, PgSE, PgDDS, PgPPDS, and PgCPR are elevated in comparison to their endogenous expression levels.

6. The recombinant yeast of claim 1, wherein the precursor is squalene or 2,3-oxidosqualene.

7. The recombinant yeast of claim 1, wherein a vector comprises the polynucleotide and expression of the polynucleotide is driven by a PGK1 promoter.

8. The recombinant yeast of claim 1, wherein the recombinant yeast comprises ginsenoside synthesizing genes encoding proteins having the sequence of SEQ ID NO:4, SEQ ID NO:5, SEQ ID NO:6, SEQ ID NO:7, and SEQ ID NO:8.

9. The recombinant yeast of claim 4, wherein the recombinant yeast is S. cerevisiae.

10. The recombinant yeast of claim 9, wherein the recombinant yeast has been recombinantly modified to express tHMG1, PgSE, PgDDS, PgPPDS, and PgCPR proteins from vector(s) comprising ginsenoside synthesizing genes.

11. The recombinant yeast of claim 10, wherein the expression of the ginsenoside synthesizing genes is driven by a Glycerol-3-Phosphate Dehydrogenase (GPD1) promoter.

12. The recombinant yeast of claim 11, wherein expression of the polynucleotide results in about a 5-fold increase in production of the ginsenoside in comparison to non-expression of the polynucleotide.

13. A method for preparing recombinant yeast with an enhanced productivity of ginsenosides compared to parent yeast, comprising transforming the recombinant yeast cell with a polynucleotide having the sequence of SEQ ID NO:1 and/or SEQ ID NO:3 such that expression of a protein encoded by the polynucleotide is increased, and wherein the protein has CPR5-like activity or ERO1-like activity in a ginsenoside-producing yeast strain relative to its endogenous expression levels.

14. The method of claim 13, wherein the ginsenoside-producing yeast strain is one or more selected from the group consisting of Panax ginseng dammarenediol-ll synthase (PgDDS), Panax ginseng cytochrome P450 CYP716A47 (PgPPDS), Panax ginseng NADPH-cytochrome P450 reductase (PgCPR), S. cerevisiae HMG-CoA reductase (tHMG1), and Panax ginseng squalene epoxidase (PgSE).

15. A method for preparing recombinant yeast with an enhanced productivity of ginsenoside precursors compared to parent yeast, comprising increasing the expression level of a protein encoded by the sequence of SEQ ID NO:1 and/or 3, and wherein the protein has CPR5-like activity or ERO1-like activity in a ginsenoside precursor-producing yeast strain relative to its endogenous expression levels.

16. The method of claim 15, wherein the ginsenoside precursor comprises squalene or 2,3-oxidosqualene.

17. A method for producing ginsenoside or a precursor thereof, comprising culturing the recombinant yeast of any one of claim 1.

* * * * *

SEQUENCE LISTING

<160> NUMBER OF SEQ ID NOS: 23

<210> SEQ ID NO 1
<211> LENGTH: 678
<212> TYPE: DNA
<213> ORGANISM: Saccharomyces cerevisiae

<400> SEQUENCE: 1

```
atgaagcttc aatttttttc ctttattacc ttatttgctt gtctcttcac aacagccatt      60
tttgcgaaag aggacacggc agaagatcct gagatcacac acaaggtcta ctttgacatt     120
aatcacggtg ataaacaaat tggtagaatt gttatgggat tgtatggtct caccacaccc     180
caaaccgttg aaaacttta ccagttgacc atttccaggg accctaagat gggttatttg      240
aactctatct tccatcgcgt tattcctaac ttcatgattc aaggtggcga tttcactcac     300
agatcaggta ttgggggtaa gtctatcttc ggaaacacgt tcaaagatga gaattttgat     360
gtcaaacatg acaaaccagg cagattgtct atggccaatc gtggtaaaaa caccaacgga     420
tcccaatttt tcatcaccac cgtcccatgc ccatggttgg acgtaagca cgttgtcttt     480 ggagaagtct tggatggtat ggacgtagtt cactacattg aaaacgttaa gaccgacagt     540
agaaatatgc ctgtaaagga agttattatt gtggaaagtg gtgaactgga aactgttcct     600
ttggacaata aagacgccgc caagctacag gaagagatca aagcggaagc tagcgaagca     660
gcccacgatg aactctaa                                                   678
```

<210> SEQ ID NO 2
<211> LENGTH: 1569
<212> TYPE: DNA
<213> ORGANISM: Saccharomyces cerevisiae

<400> SEQUENCE: 2

```
atgaagtttt ctgctggtgc cgtcctgtca tggtcctccc tgctgctcgc ctcctctgtt      60
ttcgcccaac aagaggctgt ggcccctgaa gactccgctg tcgttaagtt ggccaccgac     120
tccttcaatg agtacattca gtcgcacgac ttggtgcttg cggagttttt tgctccatgg     180
tgtggccact gtaagaacat ggctcctgaa tacgttaaag ccgccgagac tttagttgag     240
aaaaacatta ccttggccca gatcgactgt actgaaaacc aggatctgtg tatggaacac     300
aacattccag ggttcccaag cttgaagatt ttcaaaaaca gcgatgttaa caactcgatc     360
gattacgagg gacctagaac tgccgaggcc attgtccaat tcatgatcaa gcaaagccaa     420
ccggctgtcg ccgttgttgc tgatctacca gcttaccttg ctaacgagac ttttgtcact     480
ccagttatcg tccaatccgg taagattgac gccgacttca acgccacctt ttactccatg     540
gccaacaaac acttcaacga ctacgacttt gtctccgctg aaaacgcaga cgatgatttc     600
aagctttcta tttacttgcc ctccgccatg gacgagcctg tagtatacaa cggtaagaaa     660
gccgatatcg ctgacgctga tgttttgaa aaatggttgc aagtggaagc cttgccctac     720
tttggtgaaa tcgacggttc cgttttcgcc aatacgtcg aaagcggttt gcctttgggt     780
tacttattct acaatgacga ggaagaattg aagaataca agcctctctt taccgagttg     840
gccaaaaaga acagaggtct aatgaacttt gttagcatcg atgccagaaa attcggcaga     900
cacgccggca acttgaacat gaggaacaa ttccctctat tgccatcca cgacatgact     960
gaagacttga agtacggttt gcctcaactc tctgaagagg cgtttgacga attgagcgac    1020
aagatcgtgt ggagtctaa ggctattgaa tctttggtta aggacttctt gaaaggtgat    1080
gcctccccaa tcgtgaagtc ccaagagatc ttcgagaacc aagattcctc tgtcttccaa    1140
ttggtcggta gaaccatga cgaaatcgtc aacgacccaa gaaggacgt tcttgtttg    1200
tactatgccc catggtgtgg tcactgtaag agattggccc caacttacca agaactagct    1260
gatacctacg ccaacgccac atccgacgtt tgattgcta aactagacca cactgaaaac    1320
gatgtcagag gcgtcgtaat tgaaggttac ccaacaatcg tcttataccc aggtggtaag    1380
aagtccgaat ctgttgtgta ccaaggttca agatccttgg actctttatt cgacttcatc    1440
aaggaaaacg gtcacttcga cgtcgacggt aaggccttgt acgaagaagc ccaggaaaaa    1500
gctgctgagg aagccgatgc tgacgctgaa ttggctgacg aagaagatgc cattcacgat    1560
gaattgtaa                                                            1569
```

<210> SEQ ID NO 3
<211> LENGTH: 1692
<212> TYPE: DNA
<213> ORGANISM: Saccharomyces cerevisiae

<400> SEQUENCE: 3

```
atgagattaa gaaccgccat tgccacactg tgcctcacgg cttttacatc tgcaacttca      60
aacaatagct acatcgccac cgaccaaaca caaaatgcct taatgacac tcacttttgt     120
aaggtcgaca ggaatgatca cgttagtccc agttgtaacg taacattcaa tgaattaaat     180
gccataaatg aaaacattag agatgatctt tcggcgttat aaaatctga tttcttcaaa     240
tactttcggc tggatttata caagcaatgt tcattttggg acgccaacga tggtctgtgc     300
ttaaaccgcg cttgctctgt tgatgtcgta gaggactggg atacactgcc tgagtactgg     360
cagcctgaga tcttgggtag tttcaataat gatacaatga aggaagcgga tgatagcgat     420
gacgaatgta agttcttaga tcaactatgt caaaccagta aaaaacctgt agatatcgaa     480
```

-continued

```
gacaccatca actactgtga tgtaaatgac tttaacggta aaaacgccgt tctgattgat    540
ttaacagcaa atccggaacg atttacaggt tatggtggta agcaagctgg tcaaatttgg    600
tctactatct accaagacaa ctgtttaca attggcgaaa ctggtgaatc attggccaaa     660 gatgcattt  atagacttgt atccggtttc catgcctcta tcggtactca cttatcaaag    720
gaatatttga acacgaaaac tggtaaatgg agcccaatc  tggatttgtt tatggcaaga    780
atcgggaact ttcctgatag agtgacaaac atgtatttca attatgctgt tgtagctaag    840
gctctctgga aaattcaacc atatttacca gaattttcat tctgtgatct agtcaataaa    900
gaaatcaaaa acaaaatgga taacgttatt tcccagctgg acacaaaaat ttttaacgaa    960
gacttagttt ttgccaacga cctaagtttg actttgaagg acgaattcag atctcgcttc   1020
aagaatgtca cgaagattat ggattgtgtg caatgtgata gatgtagatt gtggggcaaa   1080
attcaaacta ccggttacgc aactgccttg aaaattttgt ttgaaatcaa cgacgctgat   1140
gaattcacca acaacatat  tgttggtaag ttaaccaaat atgagttgat tgcactatta   1200
caaactttcg gtagattatc tgaatctatt gaatctgtta acatgttcga aaaaatgtac   1260
gggaaaaggt taaacggttc tgaaaacagg ttaagctcat tcttccaaaa taacttcttc   1320
aacattttga aggaggcagg caagtcgatt cgttacacca tagagaacat caattccact   1380
aaagaaggaa agaaaaagac taacaattct caatcacatg tatttgatga tttaaaaatg   1440
cccaaagcag aaatagttcc aaggccctct aacggtacag taaataaatg gaagaaagct   1500
tggaatactg aagttaacaa cgttttagaa gcattcagat ttatttatag aagctatttg   1560
gatttaccca ggaacatctg ggaattatct ttgatgaagg tatacaaatt ttggaataaa   1620
ttcatcggtg ttgctgatta cgttagtgag gagacacgag agcctatttc ctataagcta   1680
gatatacaat aa                                                       1692
```

<210> SEQ ID NO 4
<211> LENGTH: 769
<212> TYPE: PRT
<213> ORGANISM: Panax ginseng

<400> SEQUENCE: 4

```
Met Trp Lys Gln Lys Gly Ala Gln Gly Asn Asp Pro Tyr Leu Tyr Ser
1               5                   10                  15

Thr Asn Asn Phe Val Gly Arg Gln Tyr Trp Glu Phe Gln Pro Asp Ala
            20                  25                  30

Gly Thr Pro Glu Glu Arg Glu Glu Val Glu Lys Ala Arg Lys Asp Tyr
        35                  40                  45

Val Asn Asn Lys Lys Leu His Gly Ile His Pro Cys Ser Asp Met Leu
    50                  55                  60

Met Arg Arg Gln Leu Ile Lys Glu Ser Gly Ile Asp Leu Leu Ser Ile
65                  70                  75                  80

Pro Pro Leu Arg Leu Asp Glu Asn Glu Gln Val Asn Tyr Asp Ala Val
                85                  90                  95

Thr Thr Ala Val Lys Lys Ala Leu Arg Leu Asn Arg Ala Ile Gln Ala
            100                 105                 110

His Asp Gly His Trp Pro Ala Glu Asn Ala Gly Ser Leu Leu Tyr Thr
        115                 120                 125

Pro Pro Leu Ile Ile Ala Leu Tyr Ile Ser Gly Thr Ile Asp Thr Ile
    130                 135                 140

Leu Thr Lys Gln His Lys Lys Glu Leu Ile Arg Phe Val Tyr Asn His
```

```
            145                 150                 155                 160
       Gln Asn Glu Asp Gly Gly Trp Gly Ser Tyr Ile Glu Gly His Ser Thr
                       165                 170                 175

Met Ile Gly Ser Val Leu Ser Tyr Val Met Leu Arg Leu Leu Gly Glu
                       180                 185                 190

Gly Leu Ala Glu Ser Asp Asp Gly Asn Gly Ala Val Glu Arg Gly Arg
                       195                 200                 205

Lys Trp Ile Leu Asp His Gly Ala Ala Gly Ile Pro Ser Trp Gly
           210                 215                 220

Lys Thr Tyr Leu Ala Val Leu Gly Val Tyr Glu Trp Glu Gly Cys Asn
       225                 230                 235                 240

Pro Leu Pro Pro Glu Phe Trp Leu Phe Pro Ser Ser Phe Pro Phe His
                       245                 250                 255

Pro Ala Lys Met Trp Ile Tyr Cys Arg Cys Thr Tyr Met Pro Met Ser
                       260                 265                 270

Tyr Leu Tyr Gly Lys Arg Tyr His Gly Pro Ile Thr Asp Leu Val Leu
                       275                 280                 285

Ser Leu Arg Gln Glu Ile Tyr Asn Ile Pro Tyr Glu Gln Ile Lys Trp
                       290                 295                 300

Asn Gln Gln Arg His Asn Cys Cys Lys Glu Asp Leu Tyr Tyr Pro His
       305                 310                 315                 320

Thr Leu Val Gln Asp Leu Val Trp Asp Gly Leu His Tyr Phe Ser Glu
                       325                 330                 335

Pro Phe Leu Lys Arg Trp Pro Phe Asn Lys Leu Arg Lys Arg Gly Leu
                       340                 345                 350

Lys Arg Val Val Glu Leu Met Arg Tyr Gly Ala Thr Glu Thr Arg Phe
                       355                 360                 365

Ile Thr Thr Gly Asn Gly Glu Lys Ala Leu Gln Ile Met Ser Trp Trp
                       370                 375                 380

Ala Glu Asp Pro Asn Gly Asp Glu Phe Lys His His Leu Ala Arg Ile
       385                 390                 395                 400

Pro Asp Phe Leu Trp Ile Ala Glu Asp Gly Met Thr Val Gln Ser Phe
                       405                 410                 415

Gly Ser Gln Leu Trp Asp Cys Ile Leu Ala Thr Gln Ala Ile Ile Ala
                       420                 425                 430

Thr Asn Met Val Glu Glu Tyr Gly Asp Ser Leu Lys Lys Ala His Phe
                       435                 440                 445

Phe Ile Lys Glu Ser Gln Ile Lys Glu Asn Pro Arg Gly Asp Phe Leu
       450                 455                 460

Lys Met Cys Arg Gln Phe Thr Lys Gly Ala Trp Thr Phe Ser Asp Gln
       465                 470                 475                 480

Asp His Gly Cys Val Val Ser Asp Cys Thr Ala Glu Ala Leu Lys Cys
                       485                 490                 495

Leu Leu Leu Leu Ser Gln Met Pro Gln Asp Ile Val Gly Glu Lys Pro
                       500                 505                 510

Glu Val Glu Arg Leu Tyr Glu Ala Val Asn Val Leu Leu Tyr Leu Gln
                       515                 520                 525

Ser Arg Val Ser Gly Gly Phe Ala Val Trp Pro Pro Val Pro Lys
                       530                 535                 540

Pro Tyr Leu Glu Met Leu Asn Pro Ser Glu Ile Phe Ala Asp Ile Val
       545                 550                 555                 560

Val Glu Arg Glu His Ile Glu Cys Thr Ala Ser Val Ile Lys Gly Leu
                       565                 570                 575
```

```
Met Ala Phe Lys Cys Leu His Pro Gly His Arg Gln Lys Glu Ile Glu
            580                 585                 590

Asp Ser Val Ala Lys Ala Ile Arg Tyr Leu Glu Arg Asn Gln Met Pro
            595                 600                 605

Asp Gly Ser Trp Tyr Gly Phe Trp Gly Ile Cys Phe Leu Tyr Gly Thr
            610                 615                 620

Phe Phe Thr Leu Ser Gly Phe Ala Ser Ala Gly Arg Thr Tyr Asp Asn
625                 630                 635                 640

Ser Glu Ala Val Arg Lys Gly Val Lys Phe Leu Ser Thr Gln Asn
                    645                 650                 655

Glu Glu Gly Gly Trp Gly Glu Ser Leu Glu Ser Cys Pro Ser Glu Lys
            660                 665                 670

Phe Thr Pro Leu Lys Gly Asn Arg Thr Asn Leu Val Gln Thr Ser Trp
            675                 680                 685

Ala Met Leu Gly Leu Met Phe Gly Gly Gln Ala Glu Arg Asp Pro Thr
            690                 695                 700

Pro Leu His Arg Ala Ala Lys Leu Leu Ile Asn Ala Gln Met Asp Asn
705                 710                 715                 720

Gly Asp Phe Pro Gln Gln Glu Ile Thr Gly Val Tyr Cys Lys Asn Ser
                    725                 730                 735

Met Leu His Tyr Ala Glu Tyr Arg Asn Ile Phe Pro Leu Trp Ala Leu
            740                 745                 750

Gly Glu Tyr Arg Lys Arg Val Trp Leu Pro Lys His Gln Leu Lys
            755                 760                 765

Ile

<210> SEQ ID NO 5
<211> LENGTH: 482
<212> TYPE: PRT
<213> ORGANISM: Panax ginseng

<400> SEQUENCE: 5

Met Val Leu Phe Phe Ser Leu Ser Leu Leu Leu Pro Leu Leu Leu
1               5                   10                  15

Leu Phe Ala Tyr Phe Ser Tyr Thr Lys Arg Ile Pro Gln Lys Glu Asn
                    20                  25                  30

Asp Ser Lys Ala Pro Leu Pro Pro Gly Gln Thr Gly Trp Pro Leu Ile
            35                  40                  45

Gly Glu Thr Leu Asn Tyr Leu Ser Cys Val Lys Ser Gly Val Ser Glu
        50                  55                  60

Asn Phe Val Lys Tyr Arg Lys Glu Lys Tyr Ser Pro Lys Val Phe Arg
65                  70                  75                  80

Thr Ser Leu Leu Gly Glu Pro Met Ala Ile Leu Cys Gly Pro Glu Gly
                    85                  90                  95

Asn Lys Phe Leu Tyr Ser Thr Glu Lys Lys Leu Val Gln Val Trp Phe
            100                 105                 110

Pro Ser Ser Val Glu Lys Met Phe Pro Arg Ser His Gly Glu Ser Asn
            115                 120                 125

Ala Asp Asn Phe Ser Lys Val Arg Gly Lys Met Met Phe Leu Leu Lys
        130                 135                 140

Val Asp Gly Met Lys Lys Tyr Val Gly Leu Met Asp Arg Val Met Lys
145                 150                 155                 160

Gln Phe Leu Glu Thr Asp Trp Asn Arg Gln Gln Ile Asn Val His
                    165                 170                 175
```

```
Asn Thr Val Lys Lys Tyr Thr Val Met Ser Cys Arg Val Phe Met
            180                 185                 190

Ser Ile Asp Asp Glu Gln Val Thr Arg Leu Gly Ser Ile Gln
            195                 200                 205

Asn Ile Glu Ala Gly Leu Leu Ala Val Pro Ile Asn Ile Pro Gly Thr
210                 215                 220

Ala Met Asn Arg Ala Ile Lys Thr Val Lys Leu Leu Thr Arg Glu Val
225                 230                 235                 240

Glu Ala Val Ile Lys Gln Arg Lys Val Asp Leu Leu Glu Asn Lys Gln
                245                 250                 255

Ala Ser Gln Pro Gln Asp Leu Leu Ser His Leu Leu Thr Ala Asn
            260                 265                 270

Gln Asp Gly Gln Phe Leu Ser Glu Ser Asp Ile Ala Ser His Leu Ile
            275                 280                 285

Gly Leu Met Gln Gly Gly Tyr Thr Thr Leu Asn Gly Thr Ile Thr Phe
290                 295                 300

Val Leu Asn Tyr Leu Ala Glu Phe Pro Asp Val Tyr Asn Gln Val Leu
305                 310                 315                 320

Lys Glu Gln Val Glu Ile Ala Asn Ser Lys His Pro Lys Glu Leu Leu
                325                 330                 335

Asn Trp Glu Asp Leu Arg Lys Met Lys Tyr Ser Trp Asn Val Ala Gln
            340                 345                 350

Glu Val Leu Arg Ile Ile Pro Pro Gly Val Gly Thr Phe Arg Glu Ala
            355                 360                 365

Ile Thr Asp Phe Thr Tyr Ala Gly Tyr Leu Ile Pro Lys Gly Trp Lys
370                 375                 380

Met His Leu Ile Pro His Asp Thr His Lys Asn Pro Thr Tyr Phe Pro
385                 390                 395                 400

Ser Pro Glu Lys Phe Asp Pro Thr Arg Phe Glu Gly Asn Gly Pro Ala
                405                 410                 415

Pro Tyr Thr Phe Thr Pro Phe Gly Gly Gly Pro Arg Met Cys Pro Gly
            420                 425                 430

Ile Glu Tyr Ala Arg Leu Val Ile Leu Ile Phe Met His Asn Val Val
            435                 440                 445

Thr Asn Phe Arg Trp Glu Lys Leu Ile Pro Asn Glu Lys Ile Leu Thr
450                 455                 460

Asp Pro Ile Pro Arg Phe Ala His Gly Leu Pro Ile His Leu His Pro
465                 470                 475                 480

His Asn

<210> SEQ ID NO 6
<211> LENGTH: 709
<212> TYPE: PRT
<213> ORGANISM: Panax ginseng

<400> SEQUENCE: 6

Met Leu Lys Val Ser Pro Phe Asp Leu Met Thr Glu Ile Leu Arg Gly
1               5                   10                  15

Gly Ser Ile Asp Pro Pro Asn Ser Ser Val Ser Ala Ala Gly Ala Ser
                20                  25                  30

Met Gln Pro Ser Leu Ala Met Leu Val Val Asn Arg Glu Leu Leu Met
            35                  40                  45

Leu Leu Thr Thr Ser Val Ala Val Leu Ile Gly Cys Val Val Val Leu
50                  55                  60
```

```
Val Trp Arg Lys Ser Ser Gln Lys His Ala Lys Ser Phe Glu Ala
 65                  70                  75                  80

Pro Lys Leu Leu Ile Pro Lys Ile Glu Pro Glu Glu Val Val Asp Asp
                 85                  90                  95

Gly Lys Lys Lys Val Thr Ile Phe Phe Gly Thr Gln Thr Gly Thr Ala
                100                 105                 110

Glu Gly Phe Ala Lys Ala Leu Ala Glu Glu Ala Lys Ala Arg Tyr Glu
                115                 120                 125

Lys Ala Ile Phe Lys Val Ile Asp Leu Asp Asp Tyr Ala Pro Glu Asp
                130                 135                 140

Asp Asp Tyr Glu Thr Lys Leu Lys Glu Ser Leu Ala Phe Phe
145                 150                 155                 160

Leu Ala Thr Tyr Gly Asp Gly Glu Pro Thr Asp Asn Ala Ala Arg Phe
                165                 170                 175

Tyr Lys Trp Phe Thr Glu Gly Lys Glu Lys Arg Glu Trp Leu Asn Asn
                180                 185                 190

Leu Gln Tyr Gly Val Phe Gly Leu Gly Asn Arg Gln Tyr Glu His Phe
                195                 200                 205

Asn Lys Ile Ala Lys Val Val Asp Asp Gly Leu Ala Glu Gln Gly Ala
210                 215                 220

Lys Arg Leu Val Pro Val Gly Met Gly Asp Asp Gln Cys Ile Glu
225                 230                 235                 240

Asp Asp Phe Thr Ala Trp Arg Glu Leu Val Trp Pro Glu Leu Asp Gln
                245                 250                 255

Leu Leu Leu Asp Glu Glu Asp Thr Ala Ala Thr Pro Tyr Thr Ala
                260                 265                 270

Ala Val Leu Glu Tyr Arg Val Val Phe His Asp Arg Thr Asp Ser Ser
                275                 280                 285

Thr Leu Leu Asn Gly Thr Thr Ser Val Ser Asn Gly His Ala Phe Tyr
                290                 295                 300

Asp Ala Gln His Pro Cys Arg Ala Asn Val Ala Val Lys Arg Glu Leu
305                 310                 315                 320

His Thr Leu Glu Ser Asp Arg Ser Cys Thr His Leu Glu Phe Asp Ile
                325                 330                 335

Ser Ser Thr Gly Leu Ala Tyr Glu Thr Gly Asp His Val Gly Val Tyr
                340                 345                 350

Thr Glu Asn Leu Ile Glu Ile Val Glu Glu Ala Glu Arg Leu Leu Ala
                355                 360                 365

Ile Ser Pro Asp Thr Tyr Phe Ser Ile His Thr Glu Lys Glu Asp Gly
                370                 375                 380

Ser Pro Val Ser Gly Ser Leu Gln Pro Pro Phe Pro Pro Cys Thr
385                 390                 395                 400

Leu Arg Glu Ala Leu Arg Arg Tyr Ala Asp Leu Leu Ser Ser Pro Lys
                405                 410                 415

Lys Ser Ala Leu Leu Ala Leu Ala Ala His Ala Ser Asp Pro Ser Glu
                420                 425                 430

Ala Asp Arg Leu Arg Phe Leu Ala Ser Pro Ala Gly Lys Asp Glu Tyr
                435                 440                 445

Ala Gln Trp Ile Val Ala Asn Gln Arg Ser Leu Leu Glu Val Leu Ala
                450                 455                 460

Glu Phe Pro Ser Ala Lys Pro Pro Leu Gly Val Phe Phe Ala Ser Val
465                 470                 475                 480
```

```
Ala Pro Arg Leu Gln Pro Arg Tyr Tyr Ser Ile Ser Ser Pro Arg
            485                 490                 495

Met Ala Pro Ser Arg Ile His Val Thr Cys Ala Leu Val Phe Glu Arg
            500                 505                 510

Thr Pro Ala Gly Arg Ile His Lys Gly Val Cys Ser Thr Trp Met Lys
            515                 520                 525

Asn Ala Val Ser Leu Glu Glu Gly Asn Asp Cys Ser Arg Ala Pro Ile
            530                 535                 540

Phe Val Arg Gln Ser Asn Phe Lys Leu Pro Ser Asp Ser Arg Met Pro
545                 550                 555                 560

Ile Ile Met Ile Gly Pro Gly Thr Gly Leu Ala Pro Phe Arg Gly Phe
                565                 570                 575

Leu Gln Glu Arg Leu Ala Leu Lys Glu Ala Gly Ala Glu Leu Gly Pro
            580                 585                 590

Ala Val Leu Tyr Phe Gly Cys Arg Asn Arg Lys Leu Asp Phe Ile Tyr
            595                 600                 605

Glu Asp Glu Leu Asn Asn Phe Val Glu Ser Gly Ala Ile Ser Glu Met
        610                 615                 620

Val Val Ala Phe Ser Arg Glu Gly Pro Thr Lys Glu Tyr Val Gln His
625                 630                 635                 640

Lys Met Ser Gln Lys Ala Ser Glu Ile Trp Asn Met Ile Ser Glu Gly
                645                 650                 655

Ala Tyr Ile Tyr Val Cys Gly Asp Ala Lys Gly Met Ala Arg Asp Val
            660                 665                 670

His Arg Thr Leu His Thr Ile Ala Gln Glu Gln Gly Ala Leu Asp Ser
            675                 680                 685

Ser Lys Ala Glu Ser Leu Val Lys Asn Leu Gln Met Thr Gly Arg Tyr
        690                 695                 700

Leu Arg Asp Val Trp
705

<210> SEQ ID NO 7
<211> LENGTH: 527
<212> TYPE: PRT
<213> ORGANISM: Saccharomyces cerevisiae

<400> SEQUENCE: 7

Met Ala Ala Asp Gln Leu Val Lys Thr Glu Val Thr Lys Lys Ser Phe
1               5                   10                  15

Thr Ala Pro Val Gln Lys Ala Ser Thr Pro Val Leu Thr Asn Lys Thr
            20                  25                  30

Val Ile Ser Gly Ser Lys Val Lys Ser Leu Ser Ser Ala Gln Ser Ser
        35                  40                  45

Ser Ser Gly Pro Ser Ser Ser Glu Glu Asp Asp Ser Arg Asp Ile
    50                  55                  60

Glu Ser Leu Asp Lys Lys Ile Arg Pro Leu Glu Glu Leu Glu Ala Leu
65                  70                  75                  80

Leu Ser Ser Gly Asn Thr Lys Gln Leu Lys Asn Lys Glu Val Ala Ala
                85                  90                  95

Leu Val Ile His Gly Lys Leu Pro Leu Tyr Ala Leu Glu Lys Lys Leu
            100                 105                 110

Gly Asp Thr Thr Arg Ala Val Ala Val Arg Arg Lys Ala Leu Ser Ile
            115                 120                 125

Leu Ala Glu Ala Pro Val Leu Ala Ser Asp Arg Leu Pro Tyr Lys Asn
        130                 135                 140
```

Tyr Asp Tyr Asp Arg Val Phe Gly Ala Cys Cys Glu Asn Val Ile Gly
145                 150                 155                 160

Tyr Met Pro Leu Pro Val Gly Val Ile Gly Pro Leu Val Ile Asp Gly
            165                 170                 175

Thr Ser Tyr His Ile Pro Met Ala Thr Thr Glu Gly Cys Leu Val Ala
        180                 185                 190

Ser Ala Met Arg Gly Cys Lys Ala Ile Asn Ala Gly Gly Ala Thr
    195                 200                 205

Thr Val Leu Thr Lys Asp Gly Met Thr Arg Gly Pro Val Val Arg Phe
210                 215                 220

Pro Thr Leu Lys Arg Ser Gly Ala Cys Lys Ile Trp Leu Asp Ser Glu
225                 230                 235                 240

Glu Gly Gln Asn Ala Ile Lys Lys Ala Phe Asn Ser Thr Ser Arg Phe
                245                 250                 255

Ala Arg Leu Gln His Ile Gln Thr Cys Leu Ala Gly Asp Leu Leu Phe
            260                 265                 270

Met Arg Phe Arg Thr Thr Thr Gly Asp Ala Met Gly Met Asn Met Ile
        275                 280                 285

Ser Lys Gly Val Glu Tyr Ser Leu Lys Gln Met Val Glu Glu Tyr Gly
    290                 295                 300

Trp Glu Asp Met Glu Val Val Ser Val Ser Gly Asn Tyr Cys Thr Asp
305                 310                 315                 320

Lys Lys Pro Ala Ala Ile Asn Trp Ile Glu Gly Arg Gly Lys Ser Val
                325                 330                 335

Val Ala Glu Ala Thr Ile Pro Gly Asp Val Val Arg Lys Val Leu Lys
            340                 345                 350

Ser Asp Val Ser Ala Leu Val Glu Leu Asn Ile Ala Lys Asn Leu Val
    355                 360                 365

Gly Ser Ala Met Ala Gly Ser Val Gly Gly Phe Asn Ala His Ala Ala
370                 375                 380

Asn Leu Val Thr Ala Val Phe Leu Ala Leu Gly Gln Asp Pro Ala Gln
385                 390                 395                 400

Asn Val Glu Ser Ser Asn Cys Ile Thr Leu Met Lys Glu Val Asp Gly
                405                 410                 415

Asp Leu Arg Ile Ser Val Ser Met Pro Ser Ile Glu Val Gly Thr Ile
            420                 425                 430

Gly Gly Gly Thr Val Leu Glu Pro Gln Gly Ala Met Leu Asp Leu Leu
    435                 440                 445

Gly Val Arg Gly Pro His Ala Thr Ala Pro Gly Thr Asn Ala Arg Gln
    450                 455                 460

Leu Ala Arg Ile Val Ala Cys Ala Val Leu Ala Gly Glu Leu Ser Leu
465                 470                 475                 480

Cys Ala Ala Leu Ala Ala Gly His Leu Val Gln Ser His Met Thr His
                485                 490                 495

Asn Arg Lys Pro Ala Glu Pro Thr Lys Pro Asn Asn Leu Asp Ala Thr
            500                 505                 510

Asp Ile Asn Arg Leu Lys Asp Gly Ser Val Thr Cys Ile Lys Ser
            515                 520                 525

<210> SEQ ID NO 8
<211> LENGTH: 545
<212> TYPE: PRT
<213> ORGANISM: Panax ginseng

<400> SEQUENCE: 8

```
Met Glu Leu Glu Arg Ser Tyr Arg Glu Asn Asp Glu Tyr Phe Leu Met
1               5                   10                  15

Phe Ala Ala Thr Leu Leu Phe Gly Phe Val Leu Tyr Leu Phe Thr Leu
            20                  25                  30

Arg Arg Arg Arg Arg Arg Glu Lys Lys Gly Gly Ala Gly Ser Met
        35                  40                  45

Glu Ile Ile Asn Gly Ala Tyr Lys Met Thr Ser Ser Ser Glu Val Asn
    50                  55                  60

Gly His Cys Thr Pro Glu Asp Ile Ala Gly Ser Ser Asp Val Ile
65                  70                  75                  80

Ile Val Gly Ala Gly Val Ala Gly Ser Ala Leu Ala Tyr Thr Leu Ala
                85                  90                  95

Lys Asp Gly Arg Arg Val His Val Ile Glu Arg Asp Leu Thr Glu Gln
                100                 105                 110

Asp Arg Ile Val Gly Glu Leu Leu Gln Pro Gly Gly Tyr Leu Lys Leu
            115                 120                 125

Val Glu Leu Gly Leu Glu Asp Cys Val Asn Glu Ile Asp Ala Gln Arg
    130                 135                 140

Val Phe Gly Tyr Ala Leu Tyr Met Asp Gly Lys Asn Thr Arg Leu Ser
145                 150                 155                 160

Tyr Pro Leu Glu Lys Phe His Ala Asp Val Ala Gly Arg Ser Phe His
                165                 170                 175

Asn Gly Arg Phe Ile Gln Arg Met Arg Glu Lys Ala Ala Ser Leu Pro
            180                 185                 190

Asn Val Arg Met Glu Gln Gly Thr Val Thr Ser Leu Val Glu Gln Lys
        195                 200                 205

Gly Thr Val Lys Gly Val Arg Tyr Lys Thr Lys Asn Gly Gln Glu Met
    210                 215                 220

Ser Ala Ala Tyr Ala Pro Leu Thr Ile Val Cys Asp Gly Cys Phe Ser
225                 230                 235                 240

Asn Leu Arg His Ser Leu Cys Asn Pro Lys Val Asp Val Pro Ser Cys
                245                 250                 255

Phe Val Gly Leu Ile Leu Glu Asn Ile Asp Leu Pro His Ile Asn His
            260                 265                 270

Gly His Val Ile Leu Ala Asp Pro Ser Pro Ile Leu Phe Tyr Lys Ile
        275                 280                 285

Ser Ser Thr Glu Ile Arg Cys Leu Val Asp Val Pro Gly Gln Lys Val
    290                 295                 300

Pro Ser Ile Ala Asn Gly Glu Leu Ala His Tyr Leu Lys Thr Ser Val
305                 310                 315                 320

Ala Pro Gln Ile Pro Pro Glu Leu Tyr Lys Ser Phe Ile Ala Ala Ile
                325                 330                 335

Asp Lys Gly Lys Ile Lys Thr Met Pro Asn Arg Ser Met Pro Ala Asp
            340                 345                 350

Pro His Ser Thr Pro Gly Ala Leu Leu Leu Gly Asp Ala Phe Asn Met
        355                 360                 365

Arg His Pro Leu Thr Gly Gly Met Thr Val Ala Leu Ser Asp Ile
    370                 375                 380

Val Leu Ile Arg Asp Leu Leu Arg Pro Leu Arg Asp Leu His Asp Ser
385                 390                 395                 400

Ser Thr Leu Cys Lys Tyr Leu Glu Ser Phe Tyr Thr Leu Arg Lys Pro
                405                 410                 415
```

```
Val Ala Ser Thr Ile Asn Thr Leu Ala Gly Ala Leu Tyr Lys Val Phe
            420                 425                 430

Cys Ala Ser Pro Asp Lys Ala Arg Gln Glu Met Arg Asp Ala Cys Phe
        435                 440                 445

Asp Tyr Leu Ser Leu Gly Gly Ile Cys Ser Glu Gly Pro Ile Ala Leu
    450                 455                 460

Leu Ser Gly Leu Asn Pro Arg Pro Met Ser Leu Phe Phe His Phe Phe
465                 470                 475                 480

Ala Val Ala Ile Tyr Gly Val Gly Arg Leu Leu Ile Pro Phe Pro Ser
                485                 490                 495

Pro Arg Lys Met Trp Leu Gly Ala Arg Leu Ile Ser Gly Ala Ser Gly
            500                 505                 510

Ile Ile Phe Pro Ile Ile Lys Ser Glu Gly Val Arg Gln Met Phe Phe
        515                 520                 525

Pro Ala Thr Val Pro Ala Tyr Tyr Arg Ala Pro Ile Thr Lys Lys
    530                 535                 540

Met
545

<210> SEQ ID NO 9
<211> LENGTH: 5535
<212> TYPE: DNA
<213> ORGANISM: Artificial Sequence
<220> FEATURE:
<223> OTHER INFORMATION: pUC57-URA3HA-PGK1 vector

<400> SEQUENCE: 9
gacgaaaggg cctcgtgata cgcctatttt tataggttaa tgtcatgata ataatggttt    60
cttagacgtc aggtggcact tttcggggaa atgtgcgcgg aaccccctatt tgtttatttt   120 tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gtttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga ccaccgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggga gtcaggcaac tatggatgaa cgaaatagac  1020
agatcgctga gataggtgcc tcactgatta agcattggta actgtcagac caagtttact  1080
catatatact ttagattgat ttaaaacttc atttttaatt taaaaggatc taggtgaaga  1140
tcctttttga taatctcatg accaaaatcc cttaacgtga gttttcgttc cactgagcgt  1200
cagaccccgt agaaaagatc aaaggatctt cttgagatcc ttttttttctg cgcgtaatct  1260
```

```
gctgcttgca aacaaaaaaa ccaccgctac cagcggtggt ttgtttgccg gatcaagagc    1320
taccaactct ttttccgaag gtaactggct tcagcagagc gcagatacca aatactgttc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acgggggttt    1560
cgtgcacaca gcccagcttg gagcgaacga cctacaccga actgagatac ctacagcgtg    1620
agctatgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttgtga tgctcgtcag    1800 gggggcggag cctatggaaa aacgccagca acgcggcctt tttacggttc ctggccttt    1860 gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
accatgatta cgccaagctt gcatgcaggc ctctgcagtc gacgggcccg tctccgggcc    2280
ccccgctagt acggccgcta ctattaagat cctcctcgga tattaacttc tgctcaccgt    2340
tgaggtcttc ctcactgatc aatttctgtt ctccattcaa gtcctcttca gaaatgagct    2400
tttgctcaga acggccgcac agctctaatt cgcggccgcc tgagtgcca ccataccacc    2460 ttttcaattc atcatttttt ttttattctt ttttttgatt tcggtttcct tgaaattttt    2520
ttgattcggt aatctccgaa cagaaggaag aacgaaggaa ggagcacaga cttagattgg    2580
tatatatacg catatgtagt gttgaagaaa catgaaattg cccagtattc ttaacccaac    2640
tgcacagaac aaaaacctgc aggaaacgaa gataaatcat gtcgaaagct acatataagg    2700
aacgtgctgc tactcatcct agtcctgttg ctgccaagct atttaatatc atgcacgaaa    2760
agcaaacaaa cttgtgtgct tcattggatg ttcgtaccac caaggaatta ctggagttag    2820
ttgaagcatt aggtcccaaa atttgtttac taaaaacaca tgtggatatc ttgactgatt    2880
tttccatgga gggcacagtt aagccgctaa aggcattatc cgccaagtac aattttttac    2940
tcttcgaaga cagaaaattt gctgacattg gtaatacagt caaattgcag tactctgcgg    3000
gtgtatacag aatagcagaa tgggcagaca ttacgaatgc acacggtgtg gtgggcccag    3060
gtattgttag cggtttgaag caggcggcag aagaagtaac aaaggaacct agaggccttt    3120
tgatgttagc agaattgtca tgcaagggct ccctatctac tggagaatat actaagggta    3180
ctgttgacat tgcgaagagc gacaaagatt ttgttatcgg ctttattgct caaagagaca    3240
tgggtggaag agatgaaggt tacgattggt tgattatgac acccggtgtg ggtttagatg    3300
acaagggaga cgcattgggt caacagtata gaaccgtgga tgatgtggtc tctacaggat    3360
ctgacattat tattgttgga agaggactat ttgcaaaggg aagggatgct aagtagagg    3420 gtgaacgtta cagaaaagca ggctgggaag catatttgag aagatgcggc cagcaaaact    3480
aaaaaactgt attataagta aatgcatgta tactaaactc acaaattaga gcttcaattt    3540
aattatatca gttattaccc tatgcggtgt gaaataccgc acagatgcgt aaggagaaaa    3600
```

```
taccgcatca ggaaattgta gcggccgcgg ggaaatccgc tagtacggcc gctactatta    3660
agatcctcct cggatattaa cttctgctca ccgttgaggt cttcctcact gatcaatttc    3720
tgttctccat tcaagtcctc ttcagaaatg agcttttgct cagaacggcc gcacagctcc    3780
aggtcgggat cggaacaaaa gctggagctc agacgcgaat ttttcgaaga agtaccttca    3840
aagaatgggg tcttatcttg ttttgcaagt accactgagc aggataataa tagaaatgat    3900
aatatactat agtagagata acgtcgatga cttcccatac tgtaattgct tttagttgtg    3960
tatttttagt gtgcaagttt ctgtaaatcg attaattttt ttttctttcc tcttttatt     4020 aaccttaatt tttattttag attcctgact tcaactcaag acgcacagat attataacat    4080
ctgcataata ggcatttgca agaattactc gtgagtaagg aaagagtgag gaactatcgc    4140
atacctgcat ttaaagatgc cgatttgggc gcgaatcctt tattttggct tcaccctcat    4200
actattatca gggccagaaa aggaagtgt ttccctcctt cttgaattga tgttaccctc     4260
ataaagcacg tggcctctta tcgagaaaga aattaccgtc gctcgtgatt tgtttgcaaa    4320
aagaacaaaa ctgaaaaaac ccagacacgc tcgacttcct gtcttcctat tgattgcagc    4380
ttccaatttc gtcacacaac aaggtcctag cgacggctca caggttttgt aacaagcaat    4440
cgaaggttct ggaatggcgg gaaagggttt agtaccacat gctatgatgc ccactgtgat    4500
ctccagagca agttcgttc gatcgtactg ttactctctc tctttcaaac agaattgtcc     4560
gaatcgtgtg acaacaacag cctgttctca cacactcttt tcttctaacc aaggggtgg     4620 tttagtttag tagaacctcg tgaaacttac atttacatat atataaactt gcataaattg    4680
gtcaatgcaa gaaatacata tttggtcttt tctaattcgt agttttcaa gttcttagat     4740 gctttctttt tctcttttt acagatcatc aaggaagtaa ttatctactt tttacaacaa     4800
atataaaaca tctagaacta gtggatcccc cgggctgcag gaattcgata tcaagcttat    4860
cgataccgtc gacctcgagt catgtaatta gttatgtcac gcttacattc acgccctccc    4920
cccacatccg ctctaaccga aaaggaagga gttagacaac ctgaagtcta ggtccctatt    4980 tatttttta tagttatgtt agtattaaga acgttattta tatttcaaat ttttctttt      5040 tttctgtaca gacgcgtgta cgcatgtaac attatactga aaaccttgct tgagaaggtt    5100
ttgggacgct cgaaggcttt aatttgcggc cggtaaattc actggccgtc gttttacaac    5160
gtcgtgactg ggaaaaccct ggcgttaccc aacttaatcg ccttgcagca catccccctt    5220
tcgccagctg gcgtaatagc gaagaggccc gcaccgatcg cccttcccaa cagttgcgca    5280
gcctgaatgg cgaatggcgc tgatgcggt atttttctcct tacgcatctg tgcggtattt     5340
cacaccgcat atggtgcact ctcagtacaa tctgctctga tgccgcatag ttaagccagc    5400
cccgacaccc gccaacaccc gctgacgcgc cctgacgggc ttgtctgctc ccggcatccg    5460
cttacagaca agctgtgacc gtctccggga gctgcatgtg tcagaggttt tcaccgtcat    5520
caccgaaacg cgcga                                                    5535
```

<210> SEQ ID NO 10
<211> LENGTH: 29
<212> TYPE: DNA
<213> ORGANISM: Artificial Sequence
<220> FEATURE:
<223> OTHER INFORMATION: PGK1 pro F

<400> SEQUENCE: 10
cgagctcaga cgcgaatttt tcgaagaag                                       29

<210> SEQ ID NO 11
<211> LENGTH: 51
<212> TYPE: DNA
<213> ORGANISM: Artificial Sequence
<220> FEATURE:
<223> OTHER INFORMATION: PGK1 pro R

<400> SEQUENCE: 11
gactagttct agatgtttta tatttgttgt aaaaagtaga taattacttc c        51

<210> SEQ ID NO 12
<211> LENGTH: 70
<212> TYPE: DNA
<213> ORGANISM: Artificial Sequence
<220> FEATURE:
<223> OTHER INFORMATION: P_CPR5 F

<400> SEQUENCE: 12
actagaagaa tttgtatctt ctgatcctgg tttaacacaa tggttatagt aggtttcccg    60
actggaaagc                                                          70

<210> SEQ ID NO 13
<211> LENGTH: 80
<212> TYPE: DNA
<213> ORGANISM: Artificial Sequence
<220> FEATURE:
<223> OTHER INFORMATION: P_CPR5 R

<400> SEQUENCE: 13
gtgaagagac aagcaaataa ggtaataaag gaaaaaatt gaagcttcat tgttttatat    60
ttgttgtaaa aagtagataa                                               80

<210> SEQ ID NO 14
<211> LENGTH: 70
<212> TYPE: DNA
<213> ORGANISM: Artificial Sequence
<220> FEATURE:
<223> OTHER INFORMATION: P_PDI1 F

<400> SEQUENCE: 14
cttataatgc ggggtgcaag cgccgcgtct aaaatttttt ttttttccat aggtttcccg    60
actggaaagc                                                          70

<210> SEQ ID NO 15
<211> LENGTH: 80
<212> TYPE: DNA
<213> ORGANISM: Artificial Sequence
<220> FEATURE:
<223> OTHER INFORMATION: P_PDI1 R

<400> SEQUENCE: 15
gcgagcagca gggaggacca tgacaggacg gcaccagcag aaaacttcat tgttttatat    60
ttgttgtaaa aagtagataa                                               80

<210> SEQ ID NO 16
<211> LENGTH: 70
<212> TYPE: DNA
<213> ORGANISM: Artificial Sequence
<220> FEATURE:
<223> OTHER INFORMATION: P_ERO1 F

<400> SEQUENCE: 16
gtaaaattgt acattattta tttcaaaata tataacagga tccctccagt aggtttcccg    60

```
actggaaagc                                                              70

<210> SEQ ID NO 17
<211> LENGTH: 80
<212> TYPE: DNA
<213> ORGANISM: Artificial Sequence
<220> FEATURE:
<223> OTHER INFORMATION: P_ER01 R

<400> SEQUENCE: 17
gatgtaaaag ccgtgaggca cagtgtggca atggcggttc ttaatctcat tgttttatat      60
ttgttgtaaa aagtagataa                                                  80

<210> SEQ ID NO 18
<211> LENGTH: 27
<212> TYPE: DNA
<213> ORGANISM: Artificial Sequence
<220> FEATURE:
<223> OTHER INFORMATION: CPR5 to PGK1 F

<400> SEQUENCE: 18
tcttctgatc ctggtttaac acaatgg                                           27

<210> SEQ ID NO 19
<211> LENGTH: 25
<212> TYPE: DNA
<213> ORGANISM: Artificial Sequence
<220> FEATURE:
<223> OTHER INFORMATION: CPR5 to PGK1 R

<400> SEQUENCE: 19
ctttcgcaaa aatggctgtt gtgaa                                             25

<210> SEQ ID NO 20
<211> LENGTH: 20
<212> TYPE: DNA
<213> ORGANISM: Artificial Sequence
<220> FEATURE:
<223> OTHER INFORMATION: PDI1 to PGK1 F

<400> SEQUENCE: 20
aagcgccgcg tctaaaattt                                                   20

<210> SEQ ID NO 21
<211> LENGTH: 20
<212> TYPE: DNA
<213> ORGANISM: Artificial Sequence
<220> FEATURE:
<223> OTHER INFORMATION: PDI1 to PGK1 R

<400> SEQUENCE: 21
gggaggacca tgacaggacg                                                   20

<210> SEQ ID NO 22
<211> LENGTH: 25
<212> TYPE: DNA
<213> ORGANISM: Artificial Sequence
<220> FEATURE:
<223> OTHER INFORMATION: ERO1 to PGK1 F

<400> SEQUENCE: 22
gtgctgtgta cacccgtaaa attgt                                             25

<210> SEQ ID NO 23
<211> LENGTH: 20
```

```
<212> TYPE: DNA
<213> ORGANISM: Artificial Sequence
<220> FEATURE:
<223> OTHER INFORMATION: ERO1 to PGK1 R

<400> SEQUENCE: 23
gaggcacagt gtggcaatgg                                               20
```